United States Patent
Shusterman

(10) Patent No.: US 7,485,095 B2
(45) Date of Patent: *Feb. 3, 2009

(54) MEASUREMENT AND ANALYSIS OF TRENDS IN PHYSIOLOGICAL AND/OR HEALTH DATA

(76) Inventor: Vladimir Shusterman, 245 Melwood Ave., Apartment 501, Pittsburgh, PA (US) 15213

( * ) Notice: Subject to any disclaimer, the term of this patent is extended or adjusted under 35 U.S.C. 154(b) by 469 days.

This patent is subject to a terminal disclaimer.

(21) Appl. No.: 11/327,546

(22) Filed: Jan. 6, 2006

(65) Prior Publication Data

US 2006/0122525 A1    Jun. 8, 2006

Related U.S. Application Data

(63) Continuation-in-part of application No. 10/816,638, filed on Apr. 2, 2004, now Pat. No. 7,343,197, which is a continuation-in-part of application No. 10/124,651, filed on Apr. 17, 2002, now Pat. No. 6,925,324, which is a continuation-in-part of application No. 09/583,668, filed on May 30, 2000, now Pat. No. 6,389,308.

(60) Provisional application No. 60/646,928, filed on Jan. 24, 2005.

(51) Int. Cl.
    *A61B 5/0402* (2006.01)
(52) U.S. Cl. .................................... 600/508
(58) Field of Classification Search .......... 600/508–521
    See application file for complete search history.

(56) References Cited

U.S. PATENT DOCUMENTS

| | | |
|---|---|---|
| 4,193,393 A | 3/1980 | Schlager |
| 4,679,144 A | 7/1987 | Cox et al. |
| 5,033,475 A | 7/1991 | Ueda et al. |
| 5,463,548 A | 10/1995 | Asada et al. |
| 5,501,229 A | 3/1996 | Selker et al. |
| 5,544,044 A | 8/1996 | Leatherman |

(Continued)

OTHER PUBLICATIONS

V. Shusterman and O. Trofimov, Building and Application of Expert Systems for Differential Diagnostics of Cardiovascular Diseases, SAMS, 1994, vol. 14, pp. 15-24.

(Continued)

*Primary Examiner*—Scott M Getzow
(74) *Attorney, Agent, or Firm*—Eckert Seamans Cherin & Mellott, LLC; David V. Radack, Esq.; David W. Brownlee, Esq.

(57) ABSTRACT

System comprised of a portable medical device and method for registering at least one of electrocardiographic (ECG), magnetocardiographic (MCG), physical activity, body position, respiration, temperature, blood pressure, vasomotor activity, blood flow, neural activity, and other physiological, and health data, extracting and representing the most significant parameters from time series (trends) of said data. The system achieves the necessary sensitivity (signal-to-noise ratio) in order to miniaturize the device by collecting data of at least one fiducial point in a cardiac complex over a period of at least one, and preferably, several seconds, and extracting the underlying typical patterns from these data. Due to the miniaturization (pocket-size), the system can be implemented in a shape of a pen (or another miniature shape) that can be worn in a pocket.

40 Claims, 13 Drawing Sheets

U.S. PATENT DOCUMENTS

| | | | |
|---|---|---|---|
| 5,594,638 | A | 1/1997 | Iliff |
| 5,724,983 | A | 3/1998 | Selker et al. |
| 5,941,820 | A | 8/1999 | Zimmerman |
| 5,956,013 | A | 9/1999 | Raj et al. |
| 5,967,995 | A | 10/1999 | Shusterman et al. |
| 6,038,469 | A | 3/2000 | Karlsson et al. |
| 6,108,635 | A | 8/2000 | Herren et al. |
| 6,126,596 | A | 10/2000 | Freedman |
| 6,188,988 | B1 | 2/2001 | Barry et al. |
| 6,236,883 | B1 * | 5/2001 | Ciaccio et al. .............. 600/515 |
| 6,480,111 | B2 | 11/2002 | Canady et al. |
| 6,681,131 | B2 | 1/2004 | Kandori et al. |
| 6,807,438 | B1 | 10/2004 | Brun Del Re et al. |
| 2004/0232912 | A1 | 11/2004 | Tsukamoto et al. |

OTHER PUBLICATIONS

William G. Baxt, MD et al., A Neural Network Aid for the Early Diagnosis of Cardiac Ischemia in Patients Presenting to the Emergency Department With Chest Pain, Annals of Emergency Medicine, Dec. 2002, pp. 575-583.

Hongmei Yan et al., The internet-based knowledge acquisition and management method to construct large-scale distrbuted medical expert systems, Computer Methods and Programs in Biomedicine (2004) 74, pp. 1-10.

Anbar, Quantitative Dynamic Telethermometry in Medical Diagnosis and Management, 1994, pp. 133-143.

Shusterman et al., Spontaneous skin temperature oscillation in normal human subjects, Amer. Physiol. Soc. 1997 pp. R1173-R1181.

Lang et al., Neuromagnetic recordings of human peripheral nerve with planar SQUID gradiometers, Phyus. Ned. Bio.. 43 1998 pp. 2379-2384.

Weinberg et al., Measuring human ventilation for apnoe detection using an optical encoder, Physiol. Meas. 1998 pp. 441-446.

Steele et al., Quantitating Physical Activity in COPD Using a Triaxial Accelerometer, Chest, May 2000 pp. 1359-1367.

Burke et al., A Micropower Dry-Electrode ECG Preamplifier, IEEE Transactions on Biomechanical Engr. vol. 47, No. 2 Feb. 2000 pp. 155-162.

Kingsley et al., Physiological Monitoring with High-Impedance Optical Electrodes (Photrodes), Conference in 2002.

Harland et al., Electric Potential probes—new directions in the remote sensing of the human body, Measurement Science and Technology vol. 13 2002 pp. 163-169.

Bison et al., Dynamical mapping of the human cardiomagnetic field with a room-temperature, laser-optical sensor, Optics Express vol. 11, No. 8 Apr. 2003 pp. 904-909.

Harland et al., High resolution ambulatory electrocardiographic monitoring using wrist-mounted electric potential sensors, Mesurement Science and Tech.vol. 14 2003 pp. 923-928.

Brink et al., A long term field exp. on aircraft noise and sleep qual. at the beginning and end of the night, The 33rd Int. Cong. and Expo. on Noise Control Engr. 2004 pp. 1-8.

Schwindt et al., Chip-scale atomic magnetometer, Applied Physics Letters vol. 85 No. 26 Dec. 2004 pp. 6409-6411.

* cited by examiner

Scale I

| Heart Rate<br>A<br>43 | Beat<br>N<br>sinus | Axis<br>N<br>60 | PR-interval<br>N<br>0.15 | P-amplitude<br>N<br>0.03 |
|---|---|---|---|---|
| QRS-duration<br>N<br>0.1 | Q-amplitude<br>N<br>0.2 | R-amplitude<br>N<br>0.8 | S-amplitude<br>N<br>0.2 | T-amplitude<br>N<br>0.3 |
| ST-segment<br>N<br>0.0 | QT-interval<br>N<br>0.4 | | | |

FIG. 3.

Scale I

| Heart Rate<br>C<br>63 | Beat<br>U<br>sinus | Axis<br>U<br>60 | PR-interval<br>U<br>0.15 | P-amplitude<br>U<br>0.03 |
|---|---|---|---|---|
| QRS-duration<br>U<br>0.1 | Q-amplitude<br>U<br>0.2 | R-amplitude<br>U<br>0.8 | S-amplitude<br>U<br>0.2 | T-amplitude<br>U<br>0.3 |
| ST-segment<br>U<br>0.0 | QT-interval<br>U<br>0.4 | | | |

FIG. 4.

| Scale I | | | | |
|---|---|---|---|---|
| Heart Rate<br>N<br>67 | Beat<br>N<br>sinus | Axis<br>N<br>50 | PR-interval<br>N<br>0.12 | P-amplitude<br>N<br>0.014 |
| QRS-duration<br>N<br>0.11 | Q-amplitude<br>A<br>0.38 | R-amplitude<br>N<br>1.0 | S-amplitude<br>N<br>0.2 | T-amplitude<br>N<br>0.1 |
| ST-segment<br>N<br>0.0 | QT-interval<br>A<br>0.58 | | | |

FIG. 9.

| Scale I | | | | |
|---|---|---|---|---|
| Heart Rate<br>U<br>67 | Beat<br><br>U<br>sinus | Axis<br><br>U<br>50 | PR-interval<br>U<br>0.12 | P-amplitude<br><br>U<br>0.014 |
| QRS-duration<br>U<br>0.11 | Q-amplitude<br>U<br>0.38 | R-amplitude<br>U<br>1.0 | S-amplitude<br>U<br>0.2 | T-amplitude<br>C<br>-0.35 |
| ST-segment<br>C<br>-0.02 | QT-interval<br>U<br>0.58 | | | |

FIG. 11.

MEASUREMENT AND ANALYSIS OF TRENDS IN PHYSIOLOGICAL AND/OR HEALTH DATA

CROSS-REFERENCE TO RELATED APPLICATIONS

This application is a continuation-in-part of application Ser. No. 10/816,638, filed Apr. 2, 2004, now U.S. Pat. No. 7,343,197, which is a continuation-in-part of application Ser. No. 10/124,651, filed Apr. 17, 2002, now U.S. Pat. No. 6,925,324, which was a continuation-in-part of application Ser. No. 09/583,668, filed May 30, 2000, now U.S. Pat. No. 6,389,308. The present application also claims the benefit of Provisional application Ser. No. 60/646,928, filed Jan. 24, 2005.

FIELD OF THE INVENTION

This invention relates to the field of non-contact measurements of physiological and health data, including electrocardiographic, magnetocardiographic, mechanocardiographic, ballistocardiographic data, physical activity, body position, blood pressure, vasomotor activity, temperature, and respiration, and more specifically to a method and apparatus, which can be miniaturized and adapted to wear in a pocket or attached to the clothes of a subject or striped around the body, or implanted under the skin for non-contact or contact measurement, analysis, and representation of trends in said data over different periods of time, including gradual, small changes that develop slowly and cannot be exposed by conventional analysis, structuring and representing the results in the form understandable both to lay public and medical professionals.

BACKGROUND OF THE INVENTION

Most of the description of the present invention has been made using in terms of electrocardiographic and magnetocardiographic data. However, the present invention is not limited to these two types of data but also applies to other physiological and health data, including temperature, respiration, blood pressure, vasomotor activity, physical activity, and body position, that can be measured by non-contact techniques and devices.

Electrocardiography (ECG) is a widely used, simple examination of cardiac electrophysiological system that consists of measuring cardiac electrical potentials. Most ECG systems require a direct contact between the recording electrodes and surface of the skin of a subject. This contact can be further enhanced by using a conducting jel, cleaning and shaving the skin under the electrodes. While these direct-contact methods and devices constitute current gold standard in ECG diagnostics, they are not practical or convenient for long-term, continuous measurements, such as measurements performed over hours or days, weeks or months. The contact systems can be tolerated usually for 24-48 hours. Longer use is problematic, because the electrodes are not convenient for long-term use and may lead to skin irritation, itching, and other skin reactions.

Recently, C J Harland, et. al. described a non-contact electrocardiographic system that can be used for continuous ambulatory monitoring (C J Harland, T D Clark and R J Prance, High resolution ambulatory electrocardiographic monitoring using wrist-mounted electric potential sensors, Meas. Sci. Technol. 14 (2003) 923-928). They describe a newly developed electric potential sensor and its application for the ambulatory monitoring of the human ECG and show that ECG can be acquired using two of these sensors mounted on each wrist. These sensitive and low-noise sensors do not require a real current conducting path in order to operate and can work without making electrical contact to the subject. Furthermore, the same group showed that the sensors can record ECG even at some distance from the skin of a subject separated by several layers of clothing (C J Harland, T D Clark and R J Prance, Electric potential probes-new directions in the remote sensing of the human body Meas. Sci. Technol. 13 (2002) 163-169). In these publications, the authors showed that the method is sensitive to different noises and artifacts and therefore, the signals require filtering. The authors also point out that the recordings were made in an electrically shielded room, which reduces the noise and interference.

Although these authors described potential applications of their system for dynamic analysis of data on a beat-by-beat basis in an ambulatory setting, they did not describe how this system can be used for analysis of longer trends, which may include dozens-to-hundreds-to-thousands of beats during the course of longer-term continuous or serial recordings. The authors do not describe the methods that can be used to prevent or reduce the problems related to the varying environmental conditions (humidity, temperature), varying physical activity, body position, and other confounding physiological and non-physiological factors that can interfere with the ECG signal. Kingsley et. al. describe non-contact high-impedance optical electrodes that can be used for ecg measurements (S. A. Kingsley, A. Sriram, A. Pollick, J. Caldwell, F. Pearce, H. Ding, Physiological monitoring with high-impedance optical electrodes (photrodes), The 23rd Annual Army Science Conference, Dec. 2-5, 2002, Orlando Fla.). The authors also describe applications of their technology for analysis of ECG on a beat-by-beat basis.

Magnetocardiography (MCG) is a well-known method for measuring electromagnetic signals of the heart, and a number of systems for measurements of MCG are known. Kandori et al. (U.S. Pat. No. 6,681,131) discloses an apparatus for measuring bio-magnetic fields that includes a plurality of magnetometers for detecting magnetic fields generated from a live body; a driving circuit for driving the magnetometers; a computer for collecting output signals of the driving circuit in the form of data representing at least one waveform of the magnetic fields generated from the live body and for performing an arithmetic processing on the data representing the waveform of magnetic fields, a display unit, and at least one signal processing circuit for processing output signals of the driving circuit. The computer further performs an arithmetic processing of first-order differentiation on the waveform of the magnetic fields in a z direction with respect to time in order to create an arrow map and a contour map. Tsukamoto (US Patent Application 20040232912) discloses a magnetic field measurement system that allows measurement of an extremely weak magnetic field (such as MCG) by efficiently canceling the external field, in which plurality of sensing magnetometers for measuring a magnetic field signal in a direction perpendicular to the center axis of a cylindrical magnetic shield are arranged in two dimensions on a plane parallel to the center axis and a reference magnetometer for measuring the external field parallel to the center axis as a reference signal on a plane perpendicular to the plane parallel to the center axis. An article entitled "Dynamical Mapping of the Human Cardiomagnetic Field with a Room-temperature, Laser-optical Sensor" by Bison et. al in Optics Express 2003, Vol. 11, pages 904-909 describes a laser-optical magnetocardiographic system, which operates at room temperatures, does not require magnetically-shielded room, and allows measurement of beat-to-beat MCG dynamics. However, all of the above-described systems require highly sensitive sensors and data acquisition system that have significant weight and size. The size of such systems is usually significantly bigger than that of a laptop computer, and therefore are not suitable to be used as a wearable device.

MCG provides essentially the same information as the more widely used electrocardiogram (ECG). The main advantage of MCG is that this method does not require direct attachment of the sensors to the skin of a subject in contrast to ECG measurements. Therefore, the non-contact MCG measurements are more convenient than the ECG measurements and can be used over prolonged time intervals, whereas the duration of ECG measurements is usually limited to a maximum of several days (due to the inconvenience of constantly attached ECG electrodes, which might lead to itching, rash, and other skin reactions when the electrodes are attached for prolonged periods of time). Furthermore, the requirement for a good contact between the ECG electrodes and the skin of a subject often requires shaving and application of special conductive gels. In contrast, non-contact MCG measurements do not require any skin preparation and can be used continuously or repeatedly for any period of time, creating a possibility for monitoring development of slow, gradual changes in the cardiac function over a period of days-weeks-months. Such slow dynamics often characterizes development of chronic cardiac disease, age-related changes, treatment effects, changes caused by physical exercises, and other behavioral, pharmacological, and physiological effects. Furthermore, the convenience of MCG measurements allows an individual (even without a medical background) to perform the measurements by him/herself, so that the device becomes a personal monitoring/diagnostic/registration/screening/check-up system, which records the data collected over prolonged periods into a personal database. Thus, these features make MCG an optimal method for screening of wide populations of people for signs of cardiac abnormalities, monitoring slow, gradual changes in the heart that develop over the course of weeks-months-years that cannot be detected during a one-time examination, examining cardiac functions in the elderly and people at risk or with a history of cardiovascular disease, and monitoring disease development, treatment effects, effects of physical activity, and other pharmacological, behavioral, physiological, and health effects on the heart.

However, MCG has been used rarely by medical professionals, because biomagnetic signals of the heart are relatively small, and their measurements requires sensitive sensors that are expensive and have a relatively large size. In particular, previously known MCG systems are based on optical, laser-optical, or superconducting quantum interference devices (SQUIDs). These devices provide an accurate measurement of MCG, but are relatively large and are not adapted to be miniaturized to a size of a device that can be wearable.

Prior art MCG systems were designed to provide an accurate representation of biomagnetic field distribution in different regions of the heart and body. However, they usually analyze an averaged cardiac complex or a few complexes. There is a need for a wearable device and system for analysis of gradual, slow serial changes in the cardiac beats over different periods of time.

SUMMARY OF THE INVENTION

This invention provides a wearable-size, portable, and easy-to-use system and method for non-contact registration, analysis, and representation of trends in physiological and health data, which include but is not limited to electrocardiographic (ECG), magnetocardiographic (MCG), ballistocardiographic, mechanocardiographic (mechanical movements of the heart) data, physical activity, blood pressure, pulse wave, vasomotor activity, body position, respiration, and temperature, extraction and representation of the most significant parameters from one or more series of cardiac beats. The non-contact registration describes methods and devices that register physiological and health data without a requirement for direct contact with a surface of the skin of a subject. For example, non-contact registration devices and sensors can be located on the clothes (shirt) of a subject, in the pocket, in a bag, or further away from the body of the subject (situated on the desk, wall, or ceiling of the room, in the car, airplane, etc.). The non-contact devices also can be placed on the surface of the skin and can operate there, but they do not require a direct contact with skin for operation.

Usage of simple and miniature sensors usually yields a low signal-to-noise ratio (SNR). This invention compensates the low SNR by collecting the data over relatively long time windows and applying mathematical transformations, such as the averaging, to process collected data, decrease the amount of noise, and extract typical patterns despite the low SNR. This invention achieves the desired increased sensitivity (signal-to-noise ratio) which permits miniaturization and reliable performance in a variety of real-life settings and environments by collecting the data over a period of at least several cardiac beats, extracting typical patterns from these data, and analyzing the trends in the data. The trends for analysis may use different time intervals, from several seconds to minutes to hours, days, weeks, months, or years. For athletes and people monitoring their cardiovascular fitness response to exercises, the time interval might be minutes-to-hours. For patients with acute cardiovascular disease, the interval might be days-to-weeks. For patients with chronic diseases, the interval might be months-to-years.

Analysis of trends has several advantages compared to a one-time recording of said data. First, a one-time examination does not provide sufficient information for a conclusion or a diagnosis. It is important to know when the changes first appeared, how and during what period they have developed, and what other events they have been associated with. When a medical professional reads an ECG or an MCG, he/she usually requests previous recordings (which may or may not be available). The system of the present invention will provide these data and the required analysis of trends in the data.

Second, a one-time ECG, MCG, and other physiological and health data may not be a "typical", characteristic data representing the dynamics over the course of 24-hours or several days. It is well-known that a white-coat syndrome (a psychological reaction of a patient to a medical professional/environment) significantly modifies cardiovascular functions and may bias the data. The system of the present invention will eliminate this bias and collect the data in natural environment over the course of prolonged periods of time, which makes the data more robust and representative of the entire range and trend of cardiac MCG and ECG signals, and other physiological and health data.

Third, analysis of said data in every second or in every cardiac beat is technically difficult and may not be accurate, particularly, when the recordings are made in ambulatory conditions with a variety of noises associated with movements, external interferences, etc. To increase robustness and accuracy of measurements of physiological data patterns, the method of this invention uses a series of data (collected over at least several seconds to several hours). The data are first, aligned by the fiducial points that represent the same phase of a physiological cycle. In case of measurement of cardiac electrical, magnetic, or mechanical activity, the physiological cycle is a cardiac cycle. In case of measurement of respiration, the physiological cycle is a respirator cycle. In case of measurement of body movement, the physiological cycle can be one step. In case of measurement of vascular activity, the physiological cycle can be one oscillation of vasomotor activity. In case of measurement of temperature, the physiological cycle is one oscillation of temperature that can have a period of seconds to minutes to hours. The physiological cycle may include only one cardiac beat or several cardiac beats that were obtained in similar conditions (for example, stress or exercises). Note that corrupted or noisy data can be automatically excluded from this process by the algorithm, and the rest of the complexes can be filtered if necessary. Then the accepted time series of said data are averaged or otherwise mathematically transformed (for example, using a linear orthogonal decomposition) to obtain a typical pattern/waveform of said data or a characteristic set of primary elements (waveforms or orthogonal coefficients/eigenvectors or wavelets), for example, the P-wave, QRS-complex, and ST-segment), that represent the most typical, characteristic electrocardiographic features of the collected series of cardiac beats during the corresponding time interval. Finally, the representative patterns/waveforms/sets of primary elements from each time interval are assembled (concatenated) into a time series for analysis of trends.

The data should be collected over at least several cardiac beats (or seconds), and preferably over at least 100 cardiac beats (seconds), and more preferably over at least 1000 to 100000 cardiac beats (seconds). The exact duration of each time interval required for extraction of the representative pattern of said data at the $1^{st}$ step of the above-described procedure depends on the sensitivity (signal-to-noise ratio, SNR) of a particular data acquisition system. The data acquisition system of this invention can use the non-contact ECG sensors described by Harland et al. or the high-impedance optical electrodes (photrodes) described by Kingsley et al., or an electric field sensor described by Brun Del Re et al. (U.S. Pat. No. 6,807,438, 2004) also known as "dry" electrode that does not require a conducting gel that enhances the contact between the skin and the electrodes (such a system with dry electrodes is described, for example, by Burke M J, Gleeson D T. A micropower dry-electrode ECG preamplifier IEEE Trans Biomed Eng. 2000 February; 47(2):155-62.) to measure the ECG signals. The data acquisition system of this invention can also measure MCG signals by using any magnetometer, including fluxgate, optical, laser-optical, or SQUID-magnetometer.

For example, a fluxgate portable sensor (product of Billingsley Magnetics, having dimensions 3 cm×3 cm×8 cm) with noise level 7 pT/sqrt(Hz) in the required spectral band (0-40 Hz) would have intrinsic noise of about 40 pT. The peak QRS signal is typically 100 pT. After 10 min of averaging (one beat per second), the signal-to-noise ratio for the peak would be more than 50, which is more than enough to discern not only the major, integral parameters, such as the R-peak, but the fine details of the MCG. Averaging with time window of a few hours will make possible to implement much smaller sensors connected as gradientometers (gradiometers). To increase the sensitivity of the system to cardiac magnetic fields, the system of the present invention can operate as a gradiometer of the $1^{st}$, $2^{nd}$, $3^{rd}$, or higher order that measure second or higher spatial derivative of the magnetic field, respectively. The gradiometer regime eliminates sensitivity to the Earth magnetic field and remote sources of magnetic field like cars, elevators, etc. Using the gradiometer regime increases sensitivity to close sources of magnetic field, such as the heart, and reduces the sensitivity to more distant sources, such as the Earth. Long-term averaging will also help to average out signals from moving cars, elevators and other random events. Because these magnetometers and the non-contact ECG sensors have different sensitivity, the averaged number of beats may vary from as few as two to thousands of beats, and preferably at least several beats.

The data acquisition system of this invention can also use ballistocardiographic or mechanocardiographic data representing mechanical movements of the heart, which can be collected with a non-contact sensor using high-frequency radio-waves or optical waves, such as the light or laser waves. The data acquisition system of this invention can also use a microphone or several microphones or other acoustic sensors to register the sounds of the heart and breathing. The data acquisition system of this invention can also measure movements and vibrations caused by the heart, blood pressure wave (pulse wave), and respiratory movements of the chest using the pressure sensors also known as the piezoelectric sensors. Application of piezoelectric sensors for measurement of blood pressure waves has been described by Shusterman V, Anderson K P, Barnea O. in the article titled "Spontaneous skin temperature oscillations in normal human subjects." Published in the Am J Physiol. 1997 September; 273(3 Pt 2):R1173-81. Such sensors are also described by M. Brink, K. Wirth, C. Schierz in their manuscript titled "A long term field experiment on aircraft noise and sleep quality at the beginning and end of the night", which was presented at The 33rd International Congress and Exposition on Noise Control Engineering, help in Prague, Czech Republic, Aug. 22, 2004.

The patterns are extracted using at least one of the following mathematical methods: averaging of the signal over a period of several cardiac beats, orthogonal and non-orthogonal decompositions, principal component analysis, mappings and projections, wavelet transform, Fourier transform, Laplace transform, and Hilbert transform, linear and non-linear correlations, linear and non-linear regression models, analysis of variance, cluster analysis, factor analysis, canonical analysis, regression and discriminant function analyses, and probabilistic methods, Bayesian probability and Mahalanobis distance, pattern recognition, methods of artificial intelligence, fuzzy logic, neural networks, expert systems, fuzzy logic, statistical estimators, and filtering techniques, neural networks, expert systems, and hybrid artificial intelligence systems. Each of these methods has a different time and frequency resolution. Since different parts of the cardiac complexes have different time duration and frequency contents, different methods can be used also in combination to extract different parts of the cardiac complexes. Alternatively, a single method, decomposing the signal into a plurality of primary elements can also be used. In particular, several different filters can be applied with different cutoff frequencies to extract QRS-complex, P-waves, and ST-segments, which have different frequency contents. For example, a high-pass, forth-order Butterworth filter with a 30 Hz cutoff frequency can be used to detect the high-frequency R-waves, where as a low-pass Butterworth filter with a frequency of 10 Hz can be used to determine and quantify the low-frequency T-wave in the ECG or MCG signal. Alternatively, different wavelet functions/coefficients can be used to extract (separate) these components. It is also possible to use an orthogonal linear decomposition, such as the Principal Component Analysis, in which different components (eigenvectors and coefficients) would represent different parts of the cardiac complexes.

In accordance with this invention, a plurality of fiducial points are determined in at least one of ECG, MCG, and other physiological data, and then the data are averaged or otherwise transformed by accepted mathematical transformations to produce the typical patterns that are represented in a form understandable to a layman and/or medical professionals. As used herein a "fiducial point" is a specific data point, such an R-peak, in a cardiac complex or some other physiological cycle (one breathing cycle, or one step of a movement cycle, or one circadian cycle, or a REM or non-REM sleep phase). The physiological cycle can include the shortest cycle (a cardiac beat) or a longer cycle (several cardiac beats collected over a period of several minutes, for example, during a stress-test, or mental stress, or physical exercise). Other examples of fiducial points include P-wave, Q-wave, and the maximum derivative of the R-wave. This system requires detection of the timing of fiducial points (such as the R-peak) marking a specific phase in the cardiac complexes and time-aligning the data by these time-points prior to averaging. The timing of the fiducial points (such as the R-peak) in the cardiac complexes can be determined by measuring at least one of the following signals: mechanical movements of the chest and other parts of the human body measured by a 1, 2, or 3-axial accelerometer, giant magnetic resistance (GMR), or another sensor determining position and movements of the chest and body, mechanical sounds of the heart, electrical signals generated by the heart, light, infrared, and ultrasound signals measuring cardiac mechanical activity. For example, Canady et al. (U.S. Pat. No. 6,480,111, 2002) discloses a method and system for physiological monitoring using a microprocessor-enhanced magnetic field sensor to measure the mechanical effects of body motion. The measurements may be used for detection of respiration, cardiac rhythms, and blood pressure. The source or detector may be made sufficiently small, and the system is sufficiently sensitive to provide output data for very small movements, such as the movements of the chest caused by the heart beat. Since the mechanical contraction of the heart follows the electrical excitation (activation) of the ventricles after a small (several millisecond-long) and relatively constant delay, the fiducial points can be detected by using the peaks of the electrocardiogram or by measuring mechanical movements of the chest caused by the mechanical contractions of the heart or by measuring the blood pressure wave initiated by the contraction of the heart.

Previously known MCG systems operate in stationary laboratory or bed-side setting, that is the position of the system is fixed in the environment during the measurements and therefore, the position of the subject is also relatively constant. Small movements of the subject during the measurements are possible, however, these movements are limited to several inches. In contrast, this invention describes an ECG or MCG system that operates in a non-stationary environment of a freely moving subject performing regular activities. Thus, the system of the present invention is fixed relative to the heart of the subject but not relative to the environment during the measurements (which can be performed over prolonged periods of time). As described above, this is made possible by a significant miniaturization of the system of the present invention (to approximately, a pocket-size, such as the size of a pen or smaller), which makes it possible to wear and carry for prolonged periods of time. Furthermore, the subject can wear two or more pen-size devices, which measure simultaneously the magnetic fields of the heart from different angles. Then the information from all devices is collected in a processing unit, which has a wireless (or wire-type connection) with the devices. This information can be used for the following purposes: analysis of the patterns of cardiac magnetic fields at different parts of the heart (for example, the device in the pre-cordial region can measure the MCG or ECG from the anterior surface of the heart, the device in the left subcubital region can measure MCG or ECG from the lateral surface of the heart, the device in the upper-left abdominal region can measure MCG or ECG in the inferior region of the heart, and the device on the left part of the back can measure the MCG or ECG from the posterior part of the heart). In addition, the information from several devices can help filter out the noise and interferences and process the MCG or ECG signals. By using the patterns that are common in all devices, the true MCG or ECG signals can be separated from noise and interferences. Furthermore, in each device, the patterns of the MCG or ECG collected and processed over a previous period of time (representing the true signal) can be used to process and filter the new, upcoming signals.

Previously known MCG systems, measure or read in detail the distribution of biomagnetic fields around the body and the heart. In contrast, the present invention uses only the most important characteristics of the MCG or ECG, such as heart rate, the amplitude, polarity, and duration of P, Q, R, S, T and U waves, ST-segment, and the intervals between the peaks (including PR, QRS, and QT intervals). Then the system of the present invention determines the trends in the data. The present system is suitable for one-time screening of individuals and populations or serial analysis of slow, gradual changes in the pattern of cardiac complexes, such as a wide QRS complex, abnormal ST-segment, QRS, P or T-wave. This invention can be used for examining the subjects at risk or with a history of cardiovascular disease, or the elderly. The system can be used also as a personal device for monitoring individual cardiovascular health and its changes due to disease development, treatment, behavioral or psychophysiological modifications, and can be worn during regular activities over any period of time (days-weeks-months).

This invention can be used over prolonged periods of time, for example, hours, during which the subject wearing the device or several pen-size devices around the chest will move freely inside or outside the house, walk on the streets, work or perform other activities. During all these activities, the wearable device (or devices) will be exposed to various sources of magnetic fields, such as commercial magnets, which will create different electromagnetic interferences with the cardiac electromagnetic fields. Therefore, the system should have a processing/filtering capability to filter out these magnetic interferences from the acquired signals or to reject some parts of the signals that are too noisy. The filtering/processing can be done by a special miniature microprocessor or a general-purpose processing unit, such as a Personal Digital Assistant (PDA, for instance, iPAQ 5550 manufactured by Hewlett-Packard) operating with the device of the present invention, The filtering/processing can be done by at least one of the following methods: averaging of the signal over a period of several cardiac beats, orthogonal and non-orthogonal decompositions, principal component analysis, mappings and projections, wavelet transform, Fourier transform, Laplace transform, and Hilbert transform, linear and non-linear correlations, linear and non-linear regression models, analysis of variance, cluster analysis, factor analysis, canonical analysis, regression and discriminant function analyses, and probabilistic methods, Bayesian probability and Mahalanobis distance, pattern recognition, methods of artificial intelligence, fuzzy logic, neural networks and expert systems, statistical estimators, and filtering techniques, neural networks, expert systems, and hybrid artificial intelligence systems.

This invention does not require attachment of electrodes to the surface of the skin and can be used as a simple diagnostic and screening tool during regular daily activities and during night-time. Importantly, the system can be worn over any periods of time and used for analysis of slow, long-term trends in cardiac electromagnetic signals that develop gradually over periods of days-weeks-months. The system can detect slowly developing changes in the pattern of ECG or MCG signals, including changes in heart rate, the amplitude, polarity, and duration of P, Q, R, S, T and U waves, ST-segment, and the intervals between the peaks (including PR, QRS, and QT intervals). Due to the miniature (pocket-size), this invention can be implemented in a shape of a pen or pens (or another miniature shape/s) that can be worn in a pocket close to the pre-cordial area. This invention is particularly useful for periodic personal self-examination for the elderly, subjects at risk or with a history of cardiovascular disease. The system also can be used to monitor slow changes in the ECG or MCG due to development of cardiovascular disease, treatment results, physical exercises, and other behavioral, environmental, psychophysiological, pharmacological, and health factors. The system may be used as a personal device for periodic self-examinations, collection of the serial data in a personal database, and analysis of serial changes.

This invention also provides methods for serial analysis and representation of changes in the ECG or MCG signals that are understandable for a lay person and are sufficiently accurate for medical diagnosis. The method of this invention is based on a structured pattern recognition and artificial intelligence approach. This approach also optimizes the flow of information along a network of personal recorders and computer servers.

This invention can utilize the methods of mathematical analysis that are described in Shusterman U.S. Pat. No. 6,389,308, the disclosure of which is incorporated herein by reference. That patent describes a method and system that uses a structured pattern-recognition approach for accurate analysis of serial changes in the ECG, including subtle, gradual changes that cannot be detected by visual inspection or simple analysis of trends. The Shusterman patent describes the optimal flow of information, which includes several levels of detail. At the $1^{st}$ level, the vital changes are determined on-site in a real time, whereas at the next level, subtle serial changes are determined using serial analysis of all previously recorded data. In addition, the system of that patent may have sensors for measuring at least one of the following signals: 1, 2, or 3-axial accelerometer or some other sensor for measuring physical activity and position of a subject, optical light or infra-red sensor for measuring cardiac mechanical activity, sonic or ultra-sonic sensors for measuring heart and lung sounds, blood flow, and blood pressure, non-invasive, non-contact sensors for measuring glucose, hemoglobin, and other biochemical, hormonal, biophysical, respiratory, genetic, proteomic, environmental, and health data. This invention can also be used for measuring other physiological data such as blood pressure, cardiac output, vascular activity, temperature, respiration, cardiac, abdominal, or breathing sounds, blood flow, hormonal concentration, neural activity, electroencephalographic activity, and other electrical, mechanic, sonic, biochemical, biophysical processes in the human body, and/or demographic, psychological, or environmental data as described in Shusterman U.S. Pat. No. 6,925,324, the disclosure of which is incorporated herein by reference.

In particular, the neural activity in the peripheral nerves can be measured by using neuromagnetic recordings as described by G. Lang, U. Shahani, A. I. Weir, P. Maas, C. M. Pegrum, and G. B. Donaldson (Neuromagnetic recordings of the human peripheral nerve with planar SQUID gradiometers, Phys. Med. Biol. 43 (1998) 2379-2384). These authors have showed that magnetic fields produced by a traveling volley in the human ulnar nerve could be successfully measured by recording of the tangential component of the magnetic field using a planar second-order gradiometer integrated with a first-order gradiometric superconducting quantum interference device (SQUID). In this application of the present invention, the sensor can be implanted under the skin in a close proximity to the nerves, in which the activity needs to be measured. Since magnetic recordings don't require direct contact with the nervous tissue, the recording can be non-contact or contact (also referred to as direct recording, because the sensor is directly positioned on the nerve). Examples of neural activity recordings include spinal cord, vagus nerve (vagal) activity, muscular, skin and other sympathetic nerve activity, peroneal, and renal nerve activity, neural activity recorded from the autonomic, sympathetic, or para-sympathetic neural ganglia, such as the stellate ganglion, or the ganglia in the heart's fat pad, trigeminal, facial nerve activity, and other cranial and peripheral nerve activity. Similarly, neural activity in the central nervous system (brain) can be tracked by measuring neuromagnetic fields from inside or outside the brain.

In accordance with the present invention, ECG or MCG data obtained from the non-contact ECG or MCG sensors, respectively, can be analyzed by use of the methods described in the Shusterman patent for analyzing ECG data. This invention analyzes slowly occurring changes in the pattern of the signal and represents the results at different levels of detail using the color-coded scales which are understandable to a lay person and a medical professional. Low, intermediate and high-resolution scales are defined according to the corresponding software and hardware resources. A low-resolution scale represents a small number of primary elements such as intervals between the heart beats, duration of PQ, QRS, and QT-intervals, amplitudes of P-, Q-, R-, S-, and T-waves. This real-time analysis is implemented in a portable device that requires minimum computational resources. The set of primary elements and their search criteria are adjusted for each ECG or MCG using intermediate or high-resolution levels. At the intermediate-resolution scale, serial changes in each of the said elements are determined using a mathematical decomposition into series of orthogonal basis functions and their coefficients. This scale is implemented using a specialized processor or a computer organizer. At the high-resolution scale, combined serial changes in all elements of the ECG or MCG are determined to provide complete information about the dynamics of the signal.

The different scales optimize the flow of information along a network of personal recorders and central servers, allow structured and complete analysis and representation of ECG or magnetocardiogram and its serial changes quantitatively for medical professionals and qualitatively for a lay patient who does not have any medical background. Structuring of the analysis is achieved by constructing the at least two, and preferably three, information scales that represent the most significant parameters at different level of detail.

Low, intermediate and high-resolution scales are defined according to the corresponding software and hardware resources. A low-resolution (Scale I) represents a small number of the most important primary elements such as intervals between the heart beats, duration of PQ, QRS, and QT-intervals, amplitudes of P-, Q-, R-, S-, and T-waves. This real-time analysis is implemented in a portable device that requires minimum computational resources. The set of primary elements and their search criteria are adjusted for each ECG or MCG utilizing computational resources of intermediate or high-resolution levels. At the intermediate-resolution (Scale II), serial changes in each of the said elements are determined using a mathematical decomposition into series of orthogonal basis functions and their coefficients. This scale is implemented using a specialized processor or a computer organizer. At the high-resolution (Scale III), serial changes in all elements of the ECG or MCG and their combinations are extracted using orthogonal mathematical decomposition to provide complete information about the dynamics of the signal. This scale is implemented using a powerful processor, a network of computers or the Internet.

Scale I may be implemented in a portable, pocket-size device, in which the signal is decomposed into a plurality of primary elements and parameters such as intervals between the heart beats, type of a cardiac complex, amplitudes and duration of P-, QRS, T-, and U-wave, QT-interval, amplitude of ST-segment. Scale I of the system provides the means for real-time electrocardiographic analysis by comparing the primary elements of ECG or MCG with reference values (individual thresholds) using the minimum computational resources. The reference values are programmed into the device based on normal values for the primary elements for the patient. Scale I includes means for adjustment of individual thresholds and criteria for rejection of noisy data. A detector of noise and error rejects the noisy data if the primary elements exceed physiologic range. Alternatively, modification of the primary elements and adjustment of their search criteria can be performed automatically at the higher-resolution Scale II or Scale III. In this case, the Scale I analysis is implemented using a programmable microprocessor that can be reprogrammed at the higher-resolution scales to account for the individual characteristics of the ECG or MCG pattern and monitoring goals. Specific sets of primary elements can be used for patients with different cardiovascular abnormalities.

Scale I can be used in two modes: static mode and dynamic mode. The static mode is used for one-time ECG or MCG examination in which the newly acquired primary elements are compared with the default reference values. The dynamic mode is used for comparison of the newly acquired primary elements and waveforms with the primary elements and waveforms that were previously acquired from the same person. The shapes of QRS, T, and P-waves are compared using cross-correlation function. A small magnitude of the difference between the two measurements permits classifying them as substantially similar and keeping only one measurement in the memory. Scale I provides sufficient information for standard, one-time, clinical ECG or MCG examination. The most significant primary elements may be represented as a color, symbol, or other easy-to-read encoding of indicators that make the results useful and understandable for a lay person and a medical professional. Each signal-indicator corresponds to a single primary element. In the static mode, the values of the indicators are preferably color-coded for a lay person into normal, moderately or severely abnormal. This representation constitutes a static screen. Alternatively, the indicators may be symbol-coded, N for normal and A for abnormal reading; they may vibrate or produce a sound output for people with vision or hearing impairments. For a medical professional, the indicators provide exact, quantitative values of the primary elements. In the dynamic mode, the indicators are preferably symbol (or color)-coded into C for changed or U for unchanged. This representation constitutes a dynamic screen.

Intermediate-resolution Scale II allows viewing the ECG or MCG with automatically determined primary elements on a display and interactive editing of the set of primary elements and their search criteria. The editing can be performed by a user or a medical professional to modify the set of characteristic points or to adjust their search criteria, and can be performed either manually or automatically by the software. The individually adjusted search criteria can then be used to re-program the Scale I analysis as described earlier.

Scale II allows accurate comparison of serial ECG or MCGs and detection of small serial changes that may be unexposed by visual inspection of the signals. This scale requires higher computational resources than Scale I and can be implemented in a specialized processor, computer organizer or a personal computer. These computational resources also allow manual entering text information about the patient into the database and specific instructions regarding adjustment of time windows, threshold values, and other variables. To perform the Scale II analysis, the primary elements from serial ECG or MCGs are stored into a database to construct the time series for each primary element. The series is decomposed into a few most significant basis functions and coefficients using Principal Component Analysis (PCA) or any other orthogonal set of basis functions. The newly acquired values of the primary elements are compared with the series of the previously obtained values. Furthermore, the changes in the series of PCA coefficients are analyzed to detect small cumulative changes in the dynamics of the series that indicate instability in the cardiac electrical activity.

High-resolution Scale III is used to analyze individual and combined changes in the primary elements; at this scale, the number of the primary variables is increased to include the entire waveform of the cardiac complexes. This allows the most sensitive and accurate detection of the small changes in the individual electrocardiographic pattern. The same PCA approach is used at this scale to expose small serial changes in the ECG or MCG recordings. Scale III requires higher computational resources compared to Scale I and Scale II; it may be implemented in a powerful processing unit such as a personal or specialized computer or a distributed network of computers or the Internet.

This invention can be used for one-time examinations by patients, medical professionals, paramedics and lay public, and for dynamic assessment of changes in cardiac electrical activity. The information can be transmitted to an external computer system or a network of computers. For a lay person, the system may also include a database explaining significance of the changes in each primary element and providing simple recommendations about the measures that has to be taken if the readings of the indicators become abnormal. These may include complete cessation of physical activity, contacting a medical professional, taking a medication, etc. More detailed recommendations might be provided for patients who have specific abnormalities or medications. These patients might require special monitoring or individual adjustment of their primary elements. For example, specific monitoring the duration of QT-interval is important in patients taking antiarrhythmic drugs that prolong QT-interval.

The system can be used as a personal one-time or serial analyzer with storage of individual historic data, adaptive adjustment of individual thresholds and assessment of changes in individual pattern of said data;

a one-time or serial analyzer for a group of people, a family or a patient group, with storage of individual historic data for each person, adjustment of individual thresholds and assessment of changes in individual patterns of said data;

exchange of information, checking, and programming of pacemaker, cardioverter-defibrillator and other implantable devices;

evaluation of the treatment efficacy, side effects and progression of the disease.

Accordingly, an object of this invention is to provide a system for analyzing physiological and health data at least at two levels of detail or resolution. Both levels of resolution are presented in simple representation that can be understood by lay persons, as well as medical professionals.

A further object of this invention is to provide an analyzing system that includes a monitoring device for receiving and analyzing physiological and health data and which includes means for communicating with an external computer to which the data can be forwarded for more complex analysis. The monitoring device can be reprogrammed by the external computer to select the primary elements of the said data that are unstable or abnormal. The low level analysis performed by the monitoring device is thus focused on the critical primary elements for that individual.

The above and other objects and advantages of this invention will be more fully understood and appreciated by reference to the following description and the drawings.

BRIEF DESCRIPTION OF THE DRAWINGS

A full understanding of the invention can be gained from the following description of the preferred embodiments when read in conjunction with the accompanying drawings in which:

FIG. 3 shows the set of indicators that represent the results of ECG or MCG analysis at Scale I both qualitatively and quantitatively in a static mode ("N" denotes normal value and "A" denotes an abnormal value of a characteristic parameter).

FIG. 4 shows the set of output indicators that represent the results of ECG or MCG analysis at Scale I both qualitatively and quantitatively in a dynamic mode ("U" represents unchanged value and "C" represents a changed value of a characteristic parameter compared to a previous recording).

FIG. 9 shows the readings from the output indicators at Scale I in the static mode for the abnormal ECG or MCG in FIG. 6 (N denotes normal value, A denotes abnormal value of a characteristic parameter compared to default values).

FIG. 11 shows the readings from the indicators at Scale I in the dynamic mode for the abnormal MCG in FIG. 9.

DESCRIPTION OF THE PREFERRED EMBODIMENTS

Figure 1:
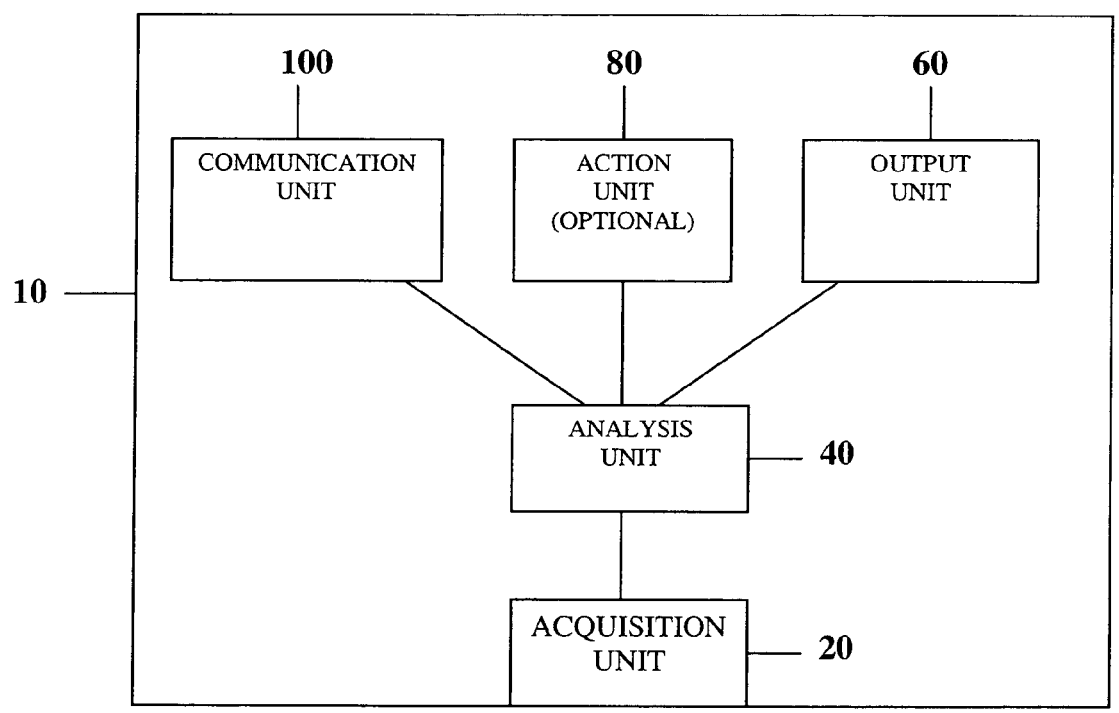
FIG. 1 is a block diagram of the medical device of the preferred embodiment of this invention.
Figure 2:
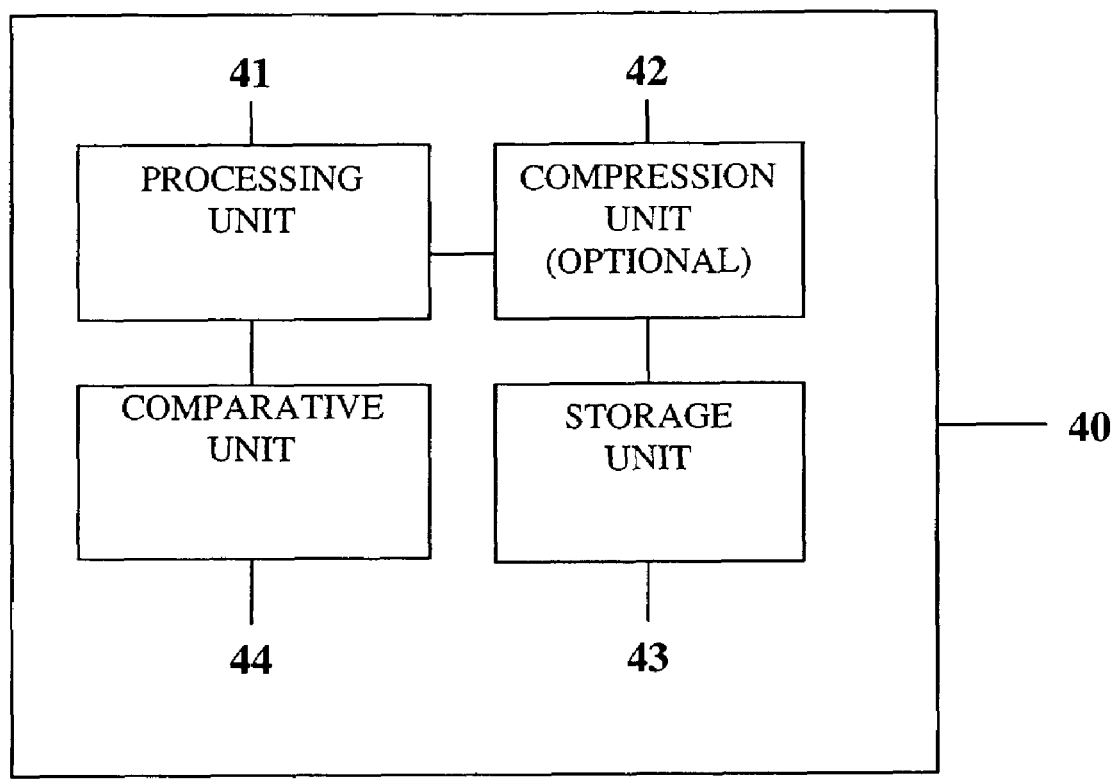
FIG. 2 is a block diagram of the analysis unit from FIG. 1.

FIG. 1 is a block-diagram of a preferred embodiment of a medical device 10 of this invention. The device consists of a non-contact acquisition unit 20 that may include at least one non-contact ECG sensor described by Harland et. al. or the high-impedance optical electrodes (photrodes) described by Kingsley et. al. to measure the ECG signals or at least one fluxgate, optical, laser-optical, or SQUID sensor for measuring the MCG, an analysis unit 40, an optional output unit 60, an action unit 80 and a communication unit 100. The acquisition part may receive ECG or MCG data from a recorded data source for analysis, but preferably receives the data real-time, on-line through the non-contact, miniature (pocket-size or smaller) sensor or multiple non-contact sensors 20 that are placed in a close proximity to a subject (in a shirt pocket or worn on a stripe around the body). As used herein, patient means an animal, and most likely a human. The medical device further includes an analysis unit or module 40 which, in turn, consists of processing, compression, storage, and comparison units (FIG. 2). The processing unit 41 can be a typical computer or personal computer of the type available from many vendors such as IBM and Hewlett-Packard. The processing unit 41 is programmed to detect a plurality of characteristic points such as the onset, peak and offset of P-, Q-, R-, S-, T-, U-waves, and computes the characteristic parameters or primary elements which include amplitudes of the said waves and ST-segment, duration of PQ-, QRS-, and QT-intervals. The processing unit 41 has a programmable microprocessor that can be programmed to modify or change the set of primary elements or to adjust their search criteria. This allows individual adjustment of the characteristic points which, in turn, increases the accuracy of detection of the primary elements. For instance, in signals with biphasic T-wave, two T-peaks should be detected, whereas monophasic T-wave requires detection of a single T-peak. Furthermore, the criteria for determining the offset of biphasic T-wave are different from the criteria for the offset of monophasic T-wave. Individual adjustment of the primary elements and their search criteria increases the accuracy of the detection of characteristic points in different ECG or MCG patterns. Still another possibility is analysis of combined changes in some primary elements or disabling analysis of the other elements. For example, in patients with possible electrolyte abnormalities, the amplitudes of the T-wave and U-wave may be combined into a single index which will be convenient for monitoring. Furthermore, the set of monitored primary elements can be modified according to the specifics of cardiovascular abnormality. For example, in patients with coronary artery disease, the amplitude and the slope of the ST-segment should be monitored continuously.

Compression unit 42 compresses the ECG or MCG waveform into a few weighted basis vectors and their coefficients using principal component analysis, wavelet decomposition, or other orthogonal mathematical transformation. Storage unit 43 stores the compressed waveforms and the computed primary elements into memory. Comparative unit 44 compares the newly acquired waveforms and newly computed primary elements with the waveforms and primary elements previously stored in the storage unit 43. The analysis unit 40 has means for adjusting the thresholds for each indicator, whereas the default values correspond to normal ECG or MCG. An output unit 60 includes a screen or a set of indicators for displaying the ECG or MCG waveforms and the computed primary elements in comparison with the previously stored primary elements or in comparison with the default reference values. The results of comparison can be represented both qualitatively and quantitatively in the dynamic and static modes. In the static mode, the quantitative representation includes exact values of the primary elements and the type of the cardiac complexes, whereas the qualitative representation includes indication of each parameter as being normal (N) or abnormal (A) as shown in FIG. 3. Abnormal readings may be further classified into moderately abnormal and severely abnormal. To make the indicators understandable to a lay person, the degree of abnormality may be color-coded: green color corresponds to a normal value, yellow corresponds to a moderate abnormality, and red corresponds to a severe abnormality. In the dynamic mode, the quantitative representation shows the differences between the newly acquired and stored primary elements and waveforms, whereas the qualitative representation includes indication of each parameter as being changed (C) or unchanged (U) as shown in FIG. 4. The output unit 60 may alternatively or additionally feed an output data to an action unit 80 for sounding an alarm, generating a vibration, or taking appropriate measures, such as applying the drugs or adjusting the therapy mode. Communication unit 100 transmits the information between the device 10 and external higher-level processing device 150. The communication unit 100 may be a modem or a wireless transmitter/receiver. Electrocardiographic signals and recorded values of primary elements and indexes are transmitted from the device 10 to higher level devices for more detailed processing and storage. The higher-level device 110 preferably transmits back to device 10 a set of primary elements and their search criteria to be used in device 10.

Figure 5:
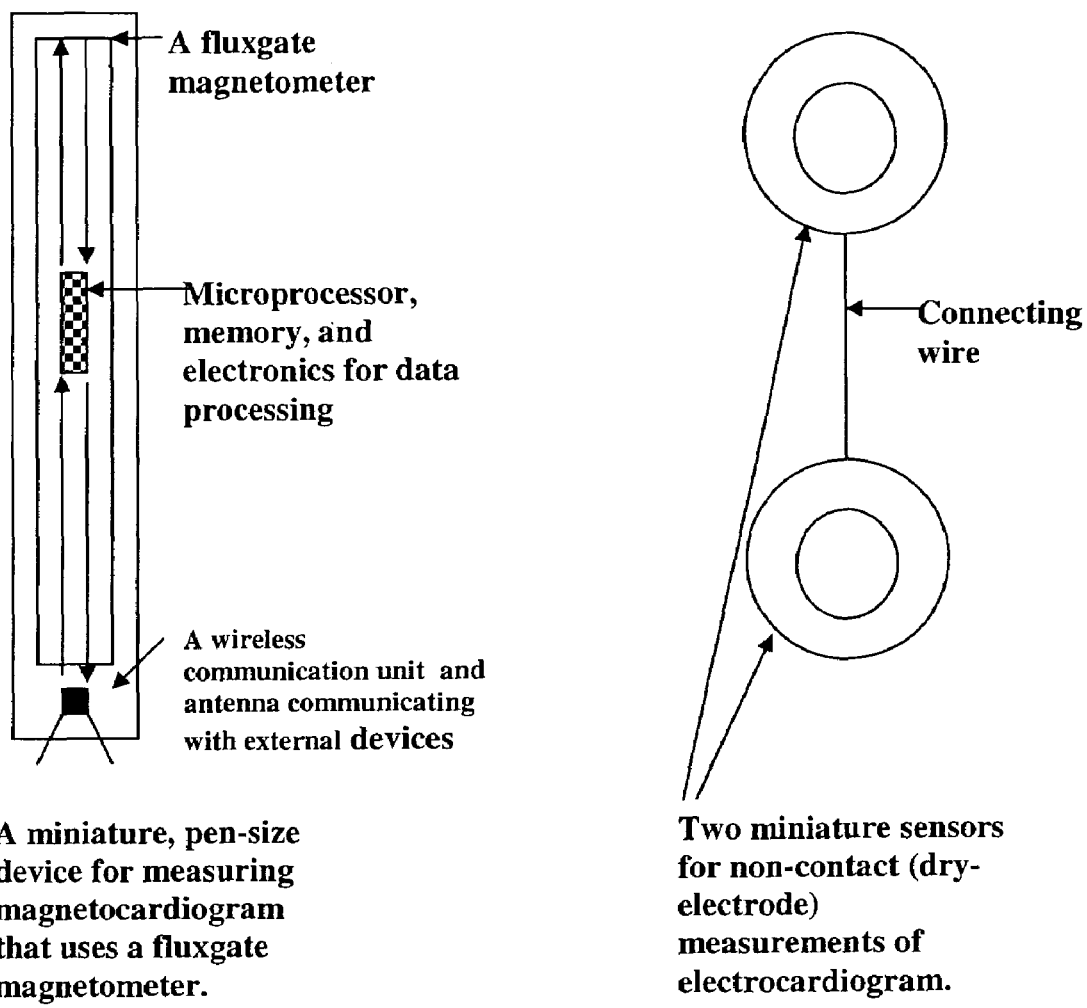
FIG. 5 is a scheme of the miniature, wearable, non-contact MCG (left) and ECG (right) measuring device.

FIG. 5 is a diagram of the miniature, wearable, non-contact MCG (left) and ECG (right) measuring device.

Figure 6:
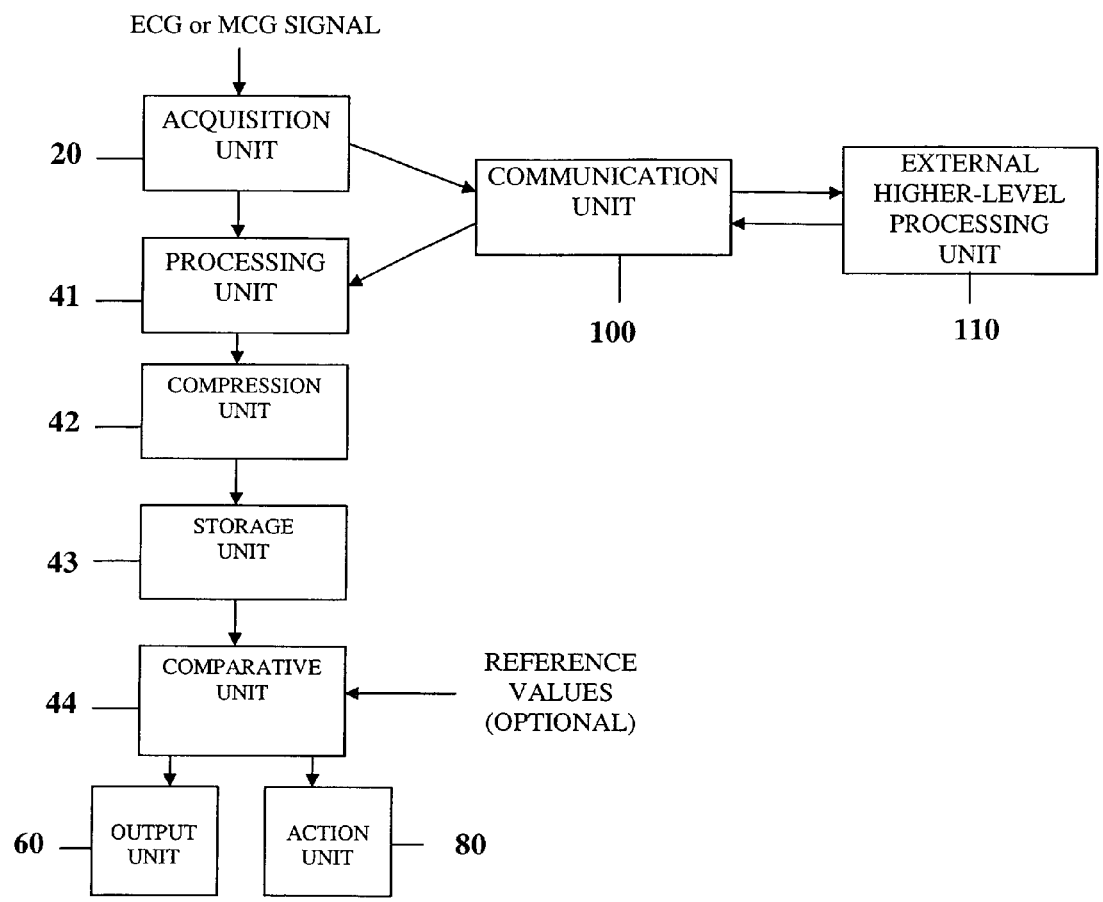
FIG. 6 is a flowchart of operation of the preferred embodiment.

FIG. 6 is a flow-chart of operation of this medical device.

Figure 7:
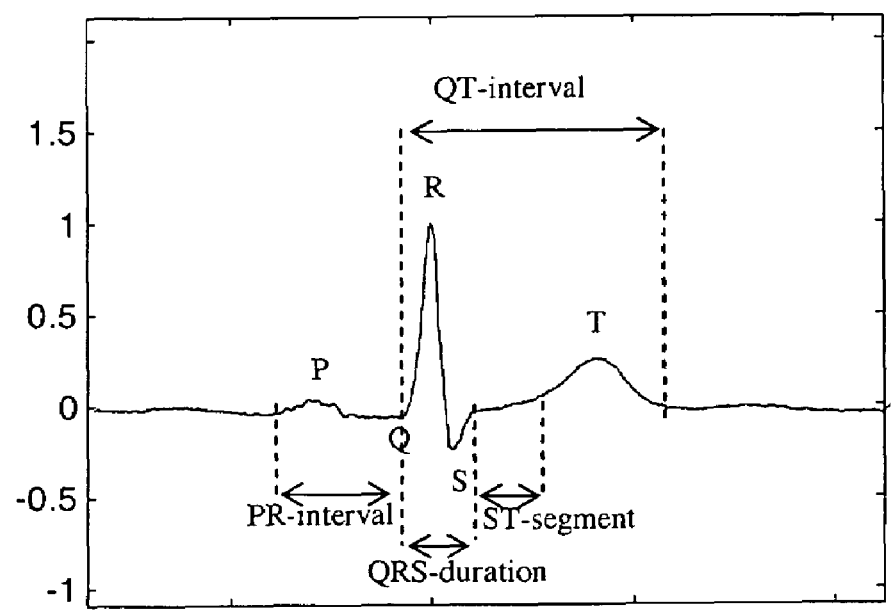
FIG. 7 is a graph of a representative ECG or magnetocardiogram from a normal subject and its segmentation into a plurality of characteristic points and segments.

FIG. 7 shows a representative ECG or MCG obtained from a normal subject and position of the characteristic points in the signal.

To achieve the optimal sensitivity in the detection of hidden or small ECG or MCG changes, a pattern recognition approach is used that extracts the basis functions from the statistics of the signal itself and gives the least error representation of the signal. Specifically, a principal component analysis (PCA) is applied which requires a minimum number of basis functions to obtain a fixed reconstruction error compared to other orthogonal expansions.

PCA is an orthogonal transformation that employs a weighted combination of several basis functions to represent a signal. The basis functions are fixed, whereas PCA-coefficients vary as a function of time. The choice of PCA for detection and characterization of the changes in ECG or MCG-signal was related to the following properties of the transform:

minimization of the mean square error within a finite number of basis functions guarantees that no other expansion will give a lower approximation error (with respect to the mean square error).

clustering transformational properties with minimization of the entropy in terms of the average squared coefficients used in the expansion.

In contrast to the methods that use fixed-form basis functions (for example, Fourier representation), basis functions in PCA are derived from the statistics of the signal. Therefore, PCA with the same number of basis functions provides a smaller residual error than other expansions.

Assume that the pattern contains M vectors $x_i$ $i=1, 2, \ldots, M$, and the length of each vector is equal to N points. To obtain the PCA coefficients, the matrix $C_x$ must be obtained using the average of the covariance matrices of x vectors. The matrix $C_x$ is defined as $$C_x = E\{(x-m_x)(x-m_x)^T\} \quad (1)$$

where $$m_x = E\{x\} \quad (2)$$

is the mean vector, and E corresponds to the expected value. Assume that the pattern of the time series has M unit-length vectors $x_i$, $i=1, 2, \ldots, M$, and the length of each vector is equal to N points, to generate a matrix $C_x$ from the outer products of vectors x. A matrix $C_x$ of M vectors $x_i$ can be calculated as $$C_x \cong \frac{1}{M}\sum_{i=1}^{M}\{(x_i - \hat{m}_x)(x_i - \hat{m}_x)^T\}, \quad (3)$$

where $i = 1, 2, \ldots M$, and $$\hat{m}_x \cong \frac{1}{M}\sum_{i=1}^{M} x_i \quad (4)$$

From the matrix $C_x$ one can obtain eigenvectors $\psi_i$, $i=1, 2, \ldots, N$ and corresponding eigenvalues $\lambda_i$, $i=1, 2, \ldots, N$. Let A be the transformation matrix whose rows are the eigenvectors of $C_x$. First eigenvector corresponds to the first eigenvalue, second one corresponds to the second eigenvalue and so on. Eigenvalues are arranged in decreasing order so that $\lambda_1 \geq \lambda_2 \geq \ldots \geq \lambda_N$. Then, PCA consists of a multiplication of the transformation matrix A by vector $(x-m_x)$:

$$y = A(x-m_x) \quad (5)$$

where y is a PCA coefficient vector. If matrix A is formed by K eigenvectors that correspond to the largest eigenvalues, y is a K×1 vector. Then, the first K coefficients contain almost entire information about the signal allowing substantial reduction in the number of analyzed coefficients and thus compression of the data. In this application, PCA is applied to the time series of each primary element, that is the intervals between the cardiac beats, duration of PQ, QRS, and QT-intervals, amplitudes of P-, Q-, R-, S-, and T-waves. For instance, to determine the characteristic pattern of the series of QT-intervals from the serial ECGs, assume that the pattern consists of M unit-length vectors $x_i$. Therefore, the series is divided into M constant-length time windows to obtain vectors $x_i$. Alternatively, the unit-length vectors $x_i$ may be comprised of a combination of all or some primary elements to determine a typical combinatorial pattern of the primary elements. Still another possibility is an extension of the concept of the unit-length vectors $x_i$ into two dimensions to represent both the combined pattern of all primary elements (in the first dimension) and the serial changes of each primary element (in the second dimension). Then PCA analysis is performed as described above.

Applications of the Principal Component Analysis at Scale II and Scale III of the System In previous works, PCA was applied for detection and classification of cardiac waveforms (QRS-complexes and ST-segments) in ECG or MCG. The optimal basis functions for QRS or ST waveforms were obtained from large training sets. PCA coefficients were used to compare individual waveforms with the set of templates and to assign the waveform to one of the classes.

Instead of applying PCA to the signal as in the previous art studies, this invention preferably applies PCA to the time series of primary elements that are extracted from the ECG or MCG-signal. This modification provides the following advantages. First, this provides an objective and accurate estimation of the serial changes in the ECG or MCG-signals and reveals small or hidden abnormalities that cannot be exposed by the previously used techniques. Second, this allows dramatic compression of the data. Third, this analysis reveals independent changes in each primary element when simultaneous changes occur in several elements. The prior art analysis of the original ECG or MCG signal might not show any changes because of the cancellation effects between the elements undergoing changes in opposite directions.

Because the time series of primary elements is nonstationary and highly variable among subjects and in the same subject over different periods of time, typical waveforms or templates of this series cannot be determined. Therefore, temporal, adaptive changes in PCA coefficients are used to detect and characterize the changes in this series. Pronounced and complex changes in the series of primary elements are identified by the simultaneous changes in several PCA coefficients. Since the basis functions in this expansion are orthogonal, simultaneous changes in several coefficients represent complex disturbances in linearly independent components of the signal. These combined changes in PCA coefficients reveal serious instabilities in the cardiac function as shown in the following examples.

The signal is separated into consecutive windows, and an array of vectors is obtained from the series. A covariance matrix is formed by the formula (3), where M is the number of vectors, x.sub.i is i.sup.th vector, and m.sub.x is calculated as in formula (4). Basis functions or eigenvectors are obtained from this matrix. Since only one covariance N.times.N matrix (N is the window length) is generated from the signal, all eigenvectors are fixed.

EXAMPLE I

The following example illustrates the sequence of ECG or MCG analysis at the system's Scales I, II and III. Serial ECG or MCG recordings from a patient A who had a structural heart disease and dynamic changes in the electrocardiogram were processed at each Scale with a different degree of detail. Scale I revealed the changes in a small number of important, primary elements using minimum computational resources. Scale II exposed changes in the primary elements that occurred in serial recordings over time. Scale III provided complete description of the serial ECG or MCG changes using a complete set of primary elements and their combinations.

Figure 8:
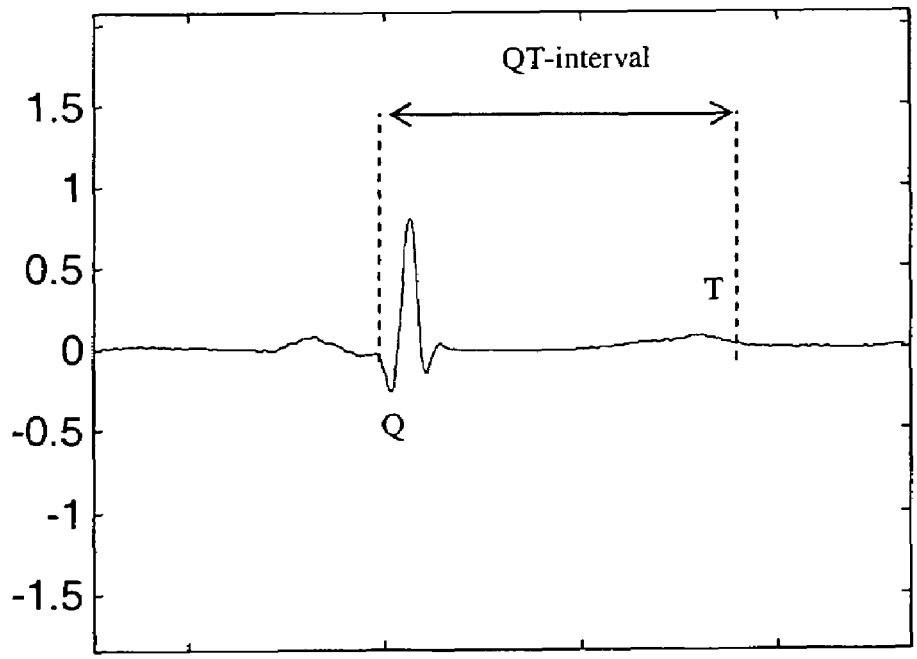
FIG. 8 is a graph of a representative ECG or MCG from a patient with a cardiac disease, large Q-wave, and prolonged QT-interval (0.5 sec) compared to the normal ECG or MCG shown in FIG. 6.

System initialization. When the system is used for the first time, initialization is required for verification and individual adjustment of the analysis criteria including identification of the primary elements and their search criteria. System initialization is performed using the hardware and software resources of the intermediate resolution Scale II and high resolution Scale III. In the initialization mode, the Scale I device transmits ECG or MCG to the higher Scale of the system via a direct or a wireless (telemetry or infrared) link. The ECG or MCG and the position of primary elements and their characteristic points (onset, peak, and offset) are visualized on a display, for example LCD display, as shown in FIG. 7. The position of characteristic points can be verified and manually edited by a user, a lay person or a medical professional. A simple manual or a software tutoring program of the typical ECG or MCG patterns, the primary elements and their characteristic points is provided for a lay person. FIG. 8 shows an ECG or MCG with a long QT-interval (0.5 sec) and a low-amplitude T-wave compared to the normal ECG or MCG shown in FIG. 7. The offset of this low-amplitude T-wave is difficult to detect automatically and a manual verification and correction are desired to ensure the accuracy. A user may also modify the set of monitored primary elements to account for a specific cardiovascular abnormality. Some of the elements may be combined into a single monitoring index, for example, a combined integral of T and U peaks can be useful for patients with possible electrolyte abnormalities.

After finishing manual verification and editing, the system automatically adjusts the search criteria for each characteristic point which include the time window, the amplitude, integral and derivative thresholds. The individually adjusted program is generated for a particular person and is automatically sent to re-program the processing sub-unit of Scale I. After the initialization, the Scale I device can work in autonomous regime without permanent connection to the higher-level Scales.

Re-initialization and serial adjustment can be performed to modify the set of primary elements and indexes and their search criteria. In addition to the procedure that was described in the system initialization, the results of the Scale II analysis can be used for serial adjustment. In particular, the primary elements and indexes whose time series and PCA coefficients demonstrate unstable behavior can be identified and included into the Scale I analysis.

Figure 10:
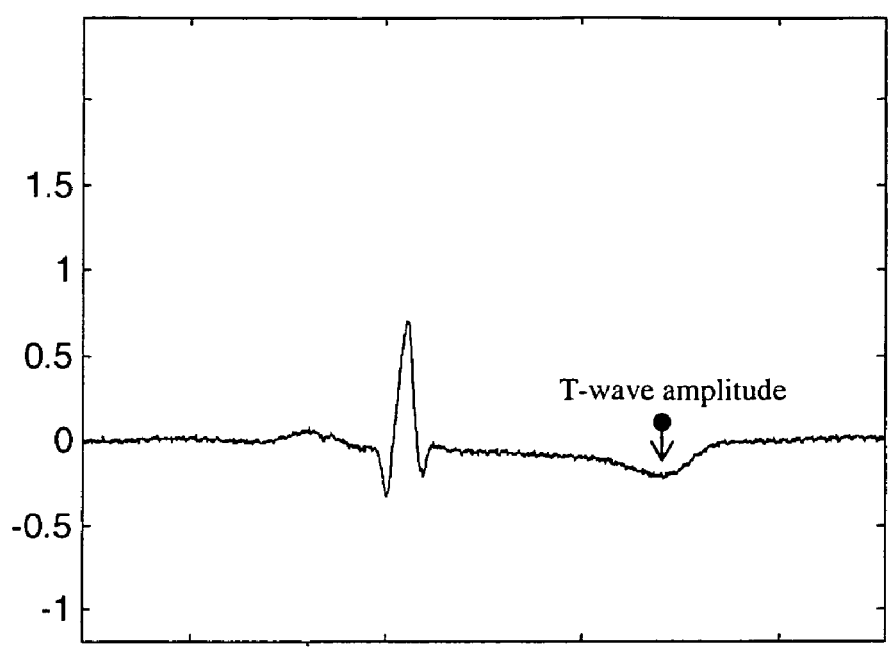
FIG. 10 is a graph of ECG or MCG obtained from the same patient as in FIG. 8 several hours later. The amplitude of T-wave decreased by 0.3 mV compared to the previous recording shown in FIG. 7.

Scale I. FIG. 8 is a graph of a representative electrocardiogram which has large Q-wave, and prolonged QT-interval. These abnormalities have been detected by the method of the present invention at the Scale I and represented qualitatively as abnormal findings and quantitatively as the exact magnitude of changes compared to the default values as shown in FIG. 9 which are readings of output indicators at Scale I for abnormal (A) and normal (N) ECG or MCG in the static mode. FIG. 10 is a graph of ECG or MCG obtained from the same patient several hours later. The amplitude of T-wave decreased by 0.3 mV compared to the previous recording shown in FIG. 9. The amplitude of T-wave decreased by 0.3 mV compared to the previous recording shown in FIG. 8. FIG. 10 shows the readings from the output indicators that represent the changes (C) in this ECG or MCG compared to the previous one.

Figure 12:
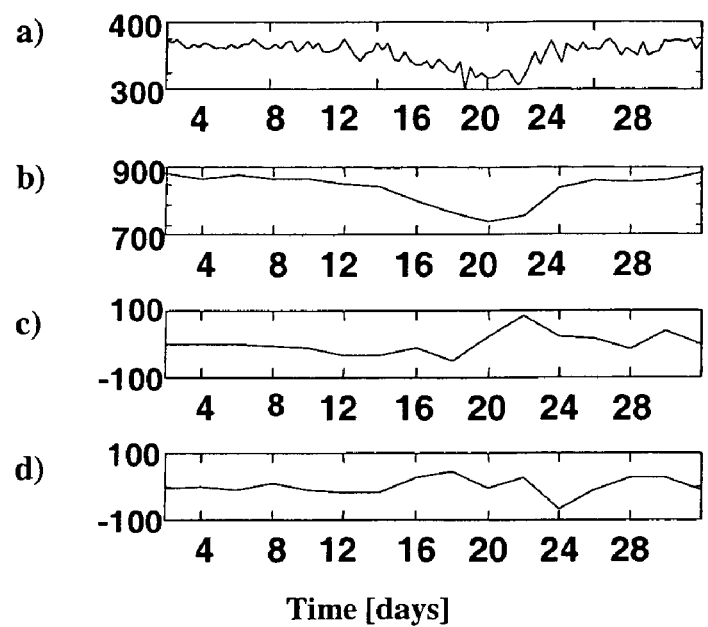
FIG. 12 shows the time series of QT-intervals (panel A) and its first three PCA-coefficients (panels B-D) in patient A during one month.
Figure 13:
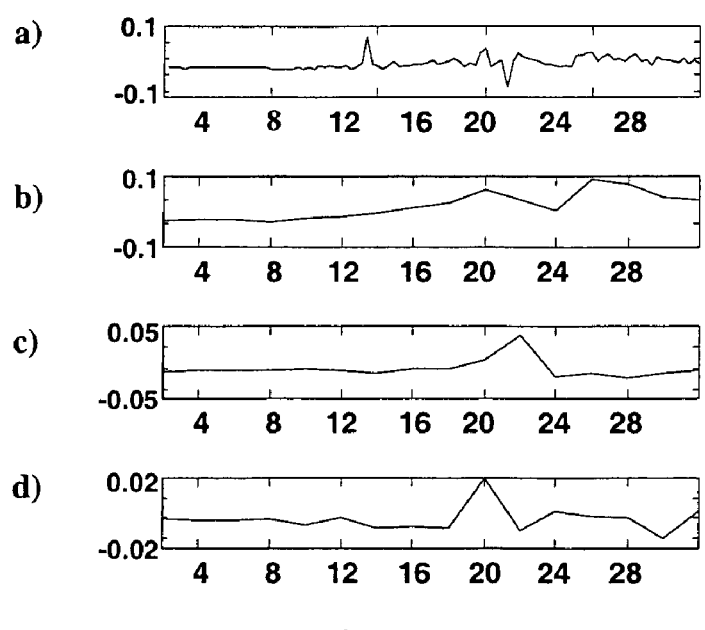
FIG. 13 shows the time series of T-wave amplitudes (panel A) and its first three PCA-coefficients (panels B-D) in patient A during one month.

Scale II. Serial ECG or MCGs have been obtained from patient A. and processed by means of Scale II to expose the time course of the serial changes that occurred in the this patient over a period of 1 month. FIG. 12, panel a, represents the series of QT-intervals that were extracted from these recordings; panels b-d demonstrate the changes in the first three PCA-coefficients that were obtained from this signal. At the end of the last recording, the patient developed a life-threatening disorder of cardiac function. However, this method reveals instability in the cardiac function as early as 20 days before the event when all known physiological indicators remain normal. FIG. 13 demonstrates changes in the T-wave amplitude extracted from the same recordings (panel a) and the corresponding first three PCA-coefficients. The time series are complex and the changes cannot be easily described or analyzed by simple tools, therefore, the changes in the signal are analyzed in a compressed form using the series of the first three PCA-coefficients which contain the most significant information about the signal. The ECG or MCG was relatively stable during the first 10 days but then became unstable as reflected by variations in the PCA-coefficients. The patient suffered a life-threatening cardiac disorder at the end of the month. However, variations in the PCA-coefficients were observed long before the event, when all physiological indicators remained normal. Calculating the changes in the variance of the PCA coefficients provides an accurate estimation of the changes and stability of the series. Unlike linear estimators such as the mean and variance of the signal or nonlinear estimators such as fractal scaling exponent or correlation dimension, disturbances in the PCA coefficients are indicative of any changes in the pattern of the signal. Therefore, analysis of PCA coefficients reveals both linear and nonlinear changes in the signal.

Figure 14:
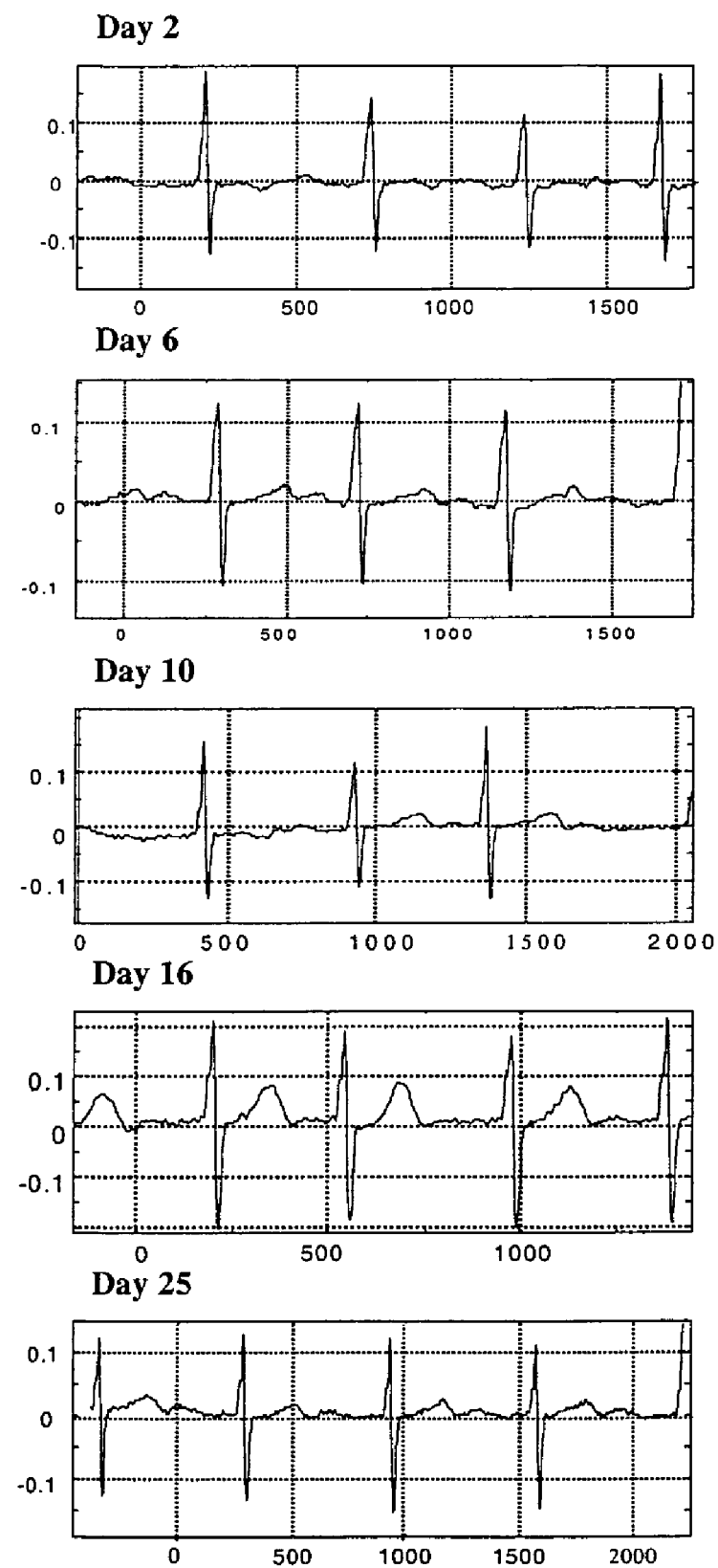
FIG. 14 shows serial MCG tracings of patient A during one month.

Scale III. The same ECG or MCGs that were analyzed at the Scales I and II, were further processed by means of Scale III to expose the entire dynamics of the ECG or MCG signal. FIG. 14 demonstrates the ECG or MCG waveforms that were obtained from serial ECG or MCG recordings in patient A. Since all the data points are included into the analysis, the changes in the shape and polarity of T-wave can be easily detected in the serial ECG or MCGs using visual inspection, PCA or other signal processing tools. The polarity of the T-waves are negative in days 2 and 10 recordings, and are positive in days 6, 16 and 25 recordings.

Figure 15:
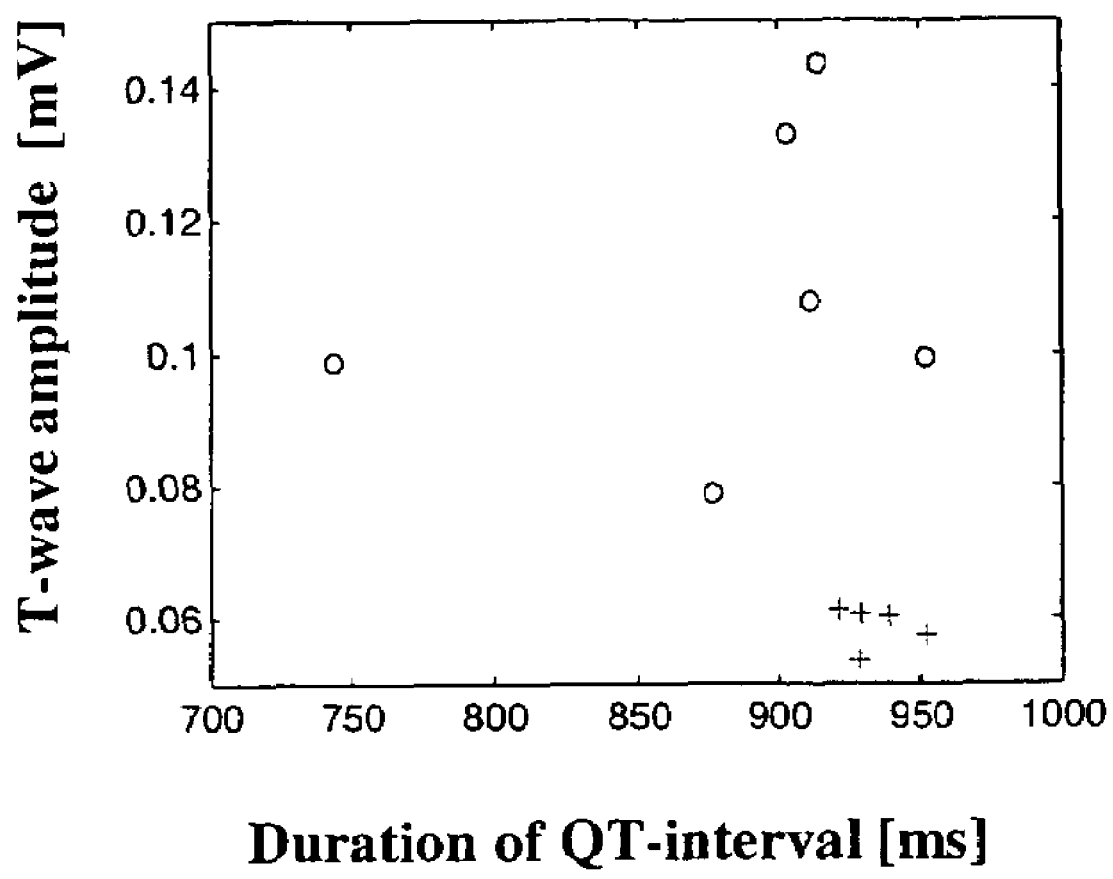
FIG. 15 is a plot of the first PCA-coefficient obtained from the series of QT-intervals versus the first PCA-coefficient obtained from the series of T-wave amplitudes in patient A.

FIG. 15 shows the changes in the PCA coefficients of these series in Scale III, dynamics of ECG or MCG in patient A in a space of the first, most significant PCA-coefficients. Y-axis represents the first PCA-coefficient that was obtained from T-wave amplitude. X-axis represents the first PCA-coefficient that was obtained from QT-interval. Each point corresponds to one-hour value. Values during 1-5 days are marked as pluses, values during 6-10 days are marked by stars, values during 11-16 days are marked by circles. Higher dispersion and change in the location of the points during 6-16 days compared to the first five days indicates instability of serial ECG or MCGs. A small cluster of data points in the lower right corner of the figure corresponds to the unchanged signals during the first 5 days of the recording. Then, the dispersion of the points increases and their location changes which reflects increased instability of the signals. Thus, the combined changes in the coefficients that were obtained from different primary elements revealed instability in the cardiac activity that preceded aggravation of the cardiac disease.

It is therefore seen that this invention provides an ECG or MCG analysis system and method for detecting a plurality of primary elements in an ECG or MCG signal, and comparing the detected signals with reference values both quantitatively and qualitatively. The outputs from the system in both low level resolution and higher levels of resolution can be understood by both lay persons and medical professionals. The system includes means for exchanging information and direction from an external computer for analysis and modification of the low resolution analysis of the signal.

EXAMPLE II

This theoretical example has been selected to show how the present invention could be implemented using a distributed network of computers with parallel processing and how it can be efficiently integrated with such methods of artificial intelligence as neural networks and expert systems to process different types of serial information obtained from a patient with chronic congestive heart failure. Patients with chronic illnesses often have a number of chronically or intermittently abnormal indicators, whose dynamics are difficult to discern. A network of computers allows fast and accurate processing of the patient's information obtained using different diagnostic techniques (such as biochemical, electrocardiographic, nuclear magnetic resonance, stress-test, and other modalities).

In a hypothetical patient B. with chronic congestive heart failure (Class II) and a three-year-old myocardial infarction, the above-described high-resolution analysis of serial ECG or MCG recordings could reveal a subtle decreasing trend in the amplitude of the ST-segment. This trend could be revealed because the serial ECG or MCG recordings were processed at the high-resolution level using a radial basis function (RBF) neural network, which was previously trained on patient's B. electrocardiographic data. Because the neural network could learn the typical patient's B. ECG or MCG pattern, it could detect subtle changes in this pattern. The magnitude of the changes may be so small and the changes so gradual, that they might escape detection by the standard ECG or MCG processing techniques, which are manually applied by the physicians or used by the current commercial ECG or MCG scanning software. The computer server, where ECG or MCG recordings from this and other patients would be stored and analyzed, would be a part of a computer network that also includes servers for analysis of biochemical, stress-test, nuclear magnetic resonance, and other data. The servers would be organized into a hybrid artificial intelligence system, which combines a neural network and expert systems. In this system, the neural networks are used where the rules of analysis can be modeled by a multi-node network structure, in which each node is assigned the specific input and output rules and connections to other nodes. On the other hand, expert systems are used when the decision making process due to numerous uncertainties is better represented by informal (heuristic) rules.

The above-described decreasing ST-amplitude trend in the serial ECG or MCG recordings lead to an activation of an expert system's rule that initiates query of other computer servers on the network that contain biochemical, stress-test, and nuclear-magnetic resonance date for the same patient. After that, the server that contained biochemical data initiates neural network analysis of the patient's enzyme level concentration for the period of time, in which ECG or MCG changes occurred. A small increasing trend is detected in the cardiac myoglobin levels, and this biochemical and ECG or MCG information are transmitted wirelessly to the personal digital assistant of an attending physician with a suggestion of a slowly developing ischemic process. The timely notification allows the physician to initiate early anti-ischemic treatment and prevent potentially life-threatening complications of the disease.

EXAMPLE III

This theoretical example is provided to show implementation of the present invention on a specialized computer network, which could be setup for individuals working in the high-demand professional environments, such as airplane pilots.

During a late-spring commercial flight, a hypothetical 46-year-old pilot suddenly developed dizziness and shortness of breath. A Scale I ECG or MCG examination showed sinus tachycardia (fast heart rates) and increased amplitude of the P-wave. The Scale I analysis is performed using a portable ECG or MCG acquisition unit, which transmitted the information wirelessly (using a Bluetooth radiofrequency communication technology to an integrated airplane health network (implemented using Wi-Fi wireless technology). A second Scale-I-device (also connected to the network) is used to examine changes in blood pressure and detected moderate increase in diastolic pressure.

The airplane integrated health system, which includes a diagnostic expert system, queries wirelessly the home network computer server of the pilot (using GPS wireless communication technology) to obtain the health data for the previous month. The home network server, in turn, activates Scale II serial analysis of all available health data and detects subtle but gradually increasing P-wave amplitude during the previous 3 days aggravated by physical exercises. In the health data file, the system also identifies information regarding the pilot's history of allergic reactions during the spring vegetation periods. This information is transmitted back to the airplane expert system, which combines the information and suggested an allergic bronchial spasm. This information is transmitted wirelessly to the personal digital assistant of an attending physician, who from his home network system sends back a recommendation of anti-allergic medication, which eliminates the symptoms.

Note that the multi-scale distributed system could be configured to operate in several different modes. In the first mode, which is activated in the airplane, the portable ECG or MCG acquisition and Scale-I-analysis unit transmits the data wirelessly to the integrated airplane health network for higher-resolution analysis. In the second mode, which is activated in a car, the portable Scale-I-analysis unit communicates wirelessly with the car computer network using a bluetooth technology. In the third mode (which is activated at home), the portable ECG or MCG acquisition and Scale-I-analysis unit transmits the data wirelessly to the home integrated computer health network (organized using Wi-Fi communication). In the fourth configuration (which is usually activated outside home, on vacations, etc.), the portable ECG or MCG acquisition and Scale-I-analysis unit transmits the data wirelessly to the personal digital assistant (PDA) or a cell phone or a smart phone (a combination of a cell phone and a PDA) for Scale II analysis. If needed, this Scale-II-analysis unit then connects wirelessly (using a cell phone GSM communication technology) to a home health computer network. Alternatively, this fourth mode of operation (with a PDA or a cell phone for Scale II analysis) could be selected to operate at home, in a car, in the airplane, and in other settings.

EXAMPLE IV

This theoretical example is selected to show application of the present invention for tracking dynamics of health data in patients with implantable cardiac devices.

A hypothetical patient with an implantable cardioverter-defibrillator has developed slowly rising average heart rate. These changes are detected by the implantable device, which transmits this information wirelessly to a home health network computer. The network computer performs serial analysis of the recordings at Scale III resolution. At the same time, the computer reaches a hospital network server and queries the recordings from the same patient during his recent hospitalization. Inclusion of these recordings into the Scale III analysis shows that a similar instability of heart rate was observed in this patient only prior to onset of life-threatening cardiac arrhythmia. Another personal device (also connected to the network) for tracking changes in blood pressure shows instability of blood pressure. An artificial intelligence system (which was integrated with the Scale III analysis) is automatically activated to interpret these findings. The system assesses the findings as clinically significant and forwards them wirelessly to a personal digital assistant of an attending physician, who decides to initiate preventive beta-blocking therapy. During the next six hours of monitoring, the Scale II and Scale III analysis shows stabilization of cardiac rhythm.

EXAMPLE V

This theoretical example describes potential benefits of the present invention in patients with congestive heart failure undergoing bi-ventricular resynchronization pacing therapy (using the implanted bi-ventricular pacing device, such as a Medtronic Insync Marquis III.™. device).

A hypothetical patient with chronic congestive heart failure undergoing resynchronization pacing for 15 months has developed a gradual increase in the QRS-duration, T-wave duration and changes in the T-wave morphology, indicative of slowly progressing repolarization heterogeneity. The thresholds were adjusted using the individual patient's reference values determined at the Scale III analysis (which was performed on a hospital health network). The results of analysis representing changes in the T-wave and QRS-duration are transmitted wirelessly to the hospital computer network for higher-resolution, in-depth processing. The Scale III analysis confirms that the magnitude of the changes exceeded 5 standard deviations never been observed in this patient previously. The information is transferred to the integrated artificial intelligence system for further interpretation. The system classifies the changes as clinically significant and forwarded them to the medical personnel. Considering these changes, a decision is made to hospitalize the patient for detailed examination and therapy adjustment.

Whereas particular aspects of the method of the present invention and particular embodiments of the invention have been described for purposes of illustration, it will be appreciated by those skilled in the art that numerous variations of the details may be made without departing from the invention as described in the appended claims. For example, two or more ECG or MCG detector devices can be used simultaneously by a patient to detect multiple fiducial points in the patient's cardiac complex. The devices would be preferably located at least several inches apart so that each device would detect signals from a different angle to the heart. For example, one device can be located in the pre-cordial region and another device can be located at the back of the body. Alternatively, the number of the devices can be increased to three or more devices, located around the chest, so that more angles are covered. The devices can be placed on a strip or another type of a material that can be wearable. The devices would preferably be in communication with one another so the multiple ECG or MCG signals that are detected can be compiled into a cumulative result. The communication between these devices can be wireless and utilize, for example the Bluetooth or Wi-Fi or other wireless communication protocols.

Examples of physiological and health data that can be registered by non-contact methods and techniques include but are not limited to temperature, body position, physical activity, and respiration. Canady et al. (U.S. Pat. No. 6,480, 111, 2002) discloses a method and system for physiological monitoring using a microprocessor-enhanced magnetic field sensor to measure the mechanical effects of body motion. The method and system described by Canady can be used for non-contact (for example, through clothes) measurements of body movements, position, movements and position of different parts of the body (arms, legs, and head), movements of the chest due to the heart beat and respiration. In addition, respiratory movements of the chest and abdomen can be registered by an elastic rubber belt placed around the chest or abdomen with a transducer that transforms mechanical stretching of the belt into electrical signals. Movements and position of the body can be measured by 1, 2, and 3-axial accelerometers, which are widely used for these purposes in different devices. For example, Steele et. al. in their manuscript titled Quantitating Physical Activity in COPD Using a Triaxial Accelerometer (B. G. Steele; L. Holt, B. Belza, S. Ferris, S. Lakshminaryan, D. M. Buchner, Chest. 2000; 117: 1359-1367.) have described such an application of triaxial accelerometer for measurement of physical activity. Other mechanical, electrical, and optical systems for non-contact measurements of physiological and health data are also a common knowledge. For example, G. M. Weinberg and J. G Webstery describe measurements of human ventilation using an optical encoder in their article titled "Measuring human ventilation for apnoea detection using an optical encoder" that was published in Physiol. Meas. 19 (1998) 441-446. Temperature data can also be measured by a non-contact infrared camera, for instance described by M. Anbar in Quantitative dynamic telethermometry in medical diagnosis and management, Boca Raton, Fla.: CRC, 1994. The method and device of the present invention can be applied for all described methods as well as other non-contact measurements of physiological and health data.

What is claimed is:

1. A method for registering at least one of electrocardiographic (EGG), magnetocardiographic (MCG), mechanocardiographic, ballistocardiographic data, physical activity, body position, respiration, temperature, blood pressure, vasomotor activity, physiological, and health data, extracting and representing the most significant parameters from series of said data, said method comprising:
   collecting said data from at least one fiducial point in a physiological cycle over a period of at least several seconds;
   analyzing said data in low-level-of-detail to extract significant features from monitored signals and compare said features with reference values, said low-level-of-detail analysis applied locally, close to the point of data acquisition; and
   analyzing said data in a higher-level-of-detail to identify at least one of short-term and long-term trends of changes in said significant features using at least one method selected from mathematical decomposition, mathematical modeling, statistical analysis, pattern recognition, and artificial intelligence.

2. A method as set forth in claim 1 in which said analyzing includes:
   collecting at least one of electrocardiographic (ECG), magnetocardiographic (MCG), ballistocardiographic, mechanocardiographic, physical activity, body position, respiration, blood pressure, vasomotor activity, temperature, physiological, and health data over a period of at least several seconds so that the minimum data collection time depends on the sensitivity (signal-to-noise ratio) of the data collection device;
   finding fiducial points indicative of a specific phase of physiological cycle;
   aligning said data using said fiducial points;
   applying a mathematical transformation to the said aligned time series of said data to obtain a typical pattern or waveform or a set of coefficients or primary elements that represent the most typical features of the said data in the corresponding time interval; and
   forming time series from the said typical patterns or waveforms or coefficients to analyze trends.

3. A method as set forth in claim 1 in which said mathematical transformation and mathematical modeling includes at least one of the following methods: averaging the signal over a period of several cardiac beats (seconds), orthogonal and non-orthogonal decompositions, principal component analysis, mappings and projections, wavelet transform, Fourier transform, Laplace transform, and Hilbert transform, linear and non-linear correlations, linear and non-linear regression models, methods of artificial intelligence, neural networks, expert systems, fuzzy logic, statistical estimators, and filtering techniques.

4. A method as set forth in claim 1, said method includes:
   detecting fiducial points indicative of a specific phase of physiological cycle;
   time-aligning the cardiac beats using said fiducial points; and
   applying said mathematical transformation to extract typical patterns from said time-aligned series of said data.

5. A method as set forth in claim 4, said detecting of fiducial points is performed by measuring at least one of the following signals: mechanical movements of the chest and other parts of the human body measured by a 1, 2, or 3 -axial accelerometer, giant magnetic resistance (GMR), transmitter and receiver of radio waves, or another sensor determining position and movements of the chest and body, mechanical sounds of the heart, electrical signals generated by the heart, light, infrared, and ultrasound signals measuring cardiac mechanical activity.

6. A method as set forth in claim 1 which includes exchanging information between said low level and said higher level of analysis to improve at least one of said levels of analysis.

7. A method for analysis of serial changes in at least one of electrocardiographic (ECG), magnetocardiographic (MCG), mechanocardiographic, ballistocardiographic data, physical activity, body position, respiration, temperature, blood pressure, vasomotor activity, physiological, and health data from a subject, said method comprising:
   registering at least one type of said data using at least one non-contact sensor over a period of at least several seconds;
   determining a typical feature comprising a pattern, waveform, set of coefficients or wavelets by applying at least one method selected from mathematical transformation, mathematical modeling, statistical analysis, pattern recognition and artificial intelligence to said at least one type of data which has been registered over a period of at least several seconds;

forming a time series from said typical feature which has been determined over a plurality of periodic time intervals;

characterizing said time series using at least one method selected from mathematical decomposition, mathematical modeling, statistical analysis, pattern recognition and artificial intelligence to generate serial characteristics indicative of changes in the subject's data; and quantifying trends in said serial characteristics using at least one method selected from mathematical transformation, mathematical modeling, statistical analysis, pattern recognition and artificial intelligence.

8. A method as set forth in claim 7 in which said mathematical transformation and mathematical modeling includes at least one of the following methods: averaging said serial changes in the cardiac beats using at least one of orthogonal and non-orthogonal decompositions, principal component analysis, mappings and projections, wavelet transform, Fourier transform, Laplace transform, and Hilbert transform, linear and non-linear correlations, linear and non-linear regression models, analysis of variance, cluster analysis, factor analysis, canonical analysis, regression and discriminant function analyses, and probabilistic methods, Bayesian probability and Mahalanobis distance, pattern recognition, methods of artificial intelligence, fuzzy logic, neural networks, expert systems, statistical estimators, filtering techniques, and hybrid artificial intelligence systems.

9. A method as said forth in claim 7 in which said
characterizing uses Principal Component Analysis (PCA) and generating PCA-coefficients indicative of both linear and nonlinear changes in the individual pattern; and
said determining the magnitude of said linear and nonlinear changes uses time varying mean and variance of said PCA-coefficients and determining the complexity of said linear and nonlinear changes by calculating the number of PCA-coefficients that exhibit substantially simultaneous changes.

10. A method as set forth in claim 7 in which said serial changes in data are communicated to a network of computers for processing and detailed analysis of the serial changes in a higher level of resolution analysis.

11. A method as set forth in claim 7 in which said registering of data occurs over a period of many days.

12. A portable system for registering at least one of electrocardiographic (ECG), magnetocardiographic (MCG), mechanocardiographic, ballistocardiographic, physical activity, body position, respiration, temperature, blood pressure, central neural activity, spinal cord activity, peripheral neural activity, cranial nerve activity, neural ganglia activity, vasomotor activity, physiological, and health data, extracting and representing the most significant parameters from series of cardiac beats, said system comprising:

at least one sensor for collecting the data for at least one fiducial point over a period of at least several seconds; and a processor for analyzing said data in at least two levels of detail to extract typical patterns from these data using a method selected from at least one of mathematical transformation, mathematical modeling, statistical analysis, pattern recognition and artificial intelligence, forming a time series from said data, extracting a typical feature comprising a pattern, waveform, set of coefficients or wavelets representing characteristic features of the said data during a plurality of time intervals, analyzing changes in said time series, and quantifying said changes.

13. A portable system as set forth in claim 12 in which said extracting of typical patterns includes:
at least one sensor for finding fiducial points indicative of specific phase of the physiological cycle; and
a processor for aligning the said data using said fiducial points and applying a mathematical transformation to the said aligned time series of said data.

14. A portable system as set forth in claim 12 in which said mathematical transformation and mathematical modeling includes at least one of the following methods: averaging the signal over a period of at least several cardiac beats, orthogonal and non-orthogonal decompositions, principal component analysis, mappings and projections, wavelet transform, Fourier transform, Laplace transform, and Hilbert transform, linear and non-linear correlations, linear and non-linear regression models, analysis of variance, cluster analysis, factor analysis, canonical analysis, regression and discriminant function analyses, and probabilistic methods, Bayesian probability and Mahalanobis distance, pattern recognition, methods of artificial intelligence, fuzzy logic, neural networks, expert systems, statistical estimators, filtering techniques, and hybrid artificial intelligence systems.

15. A portable system as set forth in claim 12 in which said mathematical transformation and mathematical modeling includes at least one of the following methods: averaging the signal over a period of at least several cardiac beats, orthogonal and non-orthogonal decompositions, principal component analysis, mappings and projections, wavelet transform, Fourier transform, Laplace transform, and Hubert transform, linear and non-linear correlations, linear and non-linear regression models, analysis of variance, cluster analysis, factor analysis, canonical analysis, regression and discriminant function analyses, and probabilistic methods, Bayesian probability and Mahalanobis distance, pattern recognition, methods of artificial intelligence, fuzzy logic, neural networks and expert systems, statistical estimators, filtering techniques, and hybrid artificial intelligence systems.

16. A portable system as set forth in claim 15, in which said processor detects fiducial points by measuring at least one of the following signals: mechanical movements of the chest and other parts of the human body measured by a 1, 2, or 3-axial accelerometer, giant magnetic resistance (GMR), optical sensor, transmitter and receiver of radio waves, or another sensor determining position and movements of the chest and body, mechanical sounds of the heart, electrical signals generated by the heart, light, infrared, and ultrasound signals measuring cardiac mechanical activity.

17. A portable system as set forth in claim 12 in which said processor
forms a time series from said serial changes;
characterizes said time series using Principal Component Analysis (PCA) and generating PCA-coefficients indicative of both linear and nonlinear changes in the individual pattern; and
determines the magnitude of said linear and nonlinear changes by using time varying mean and variance of said PCA-coefficients and determining the complexity of said linear and nonlinear changes by calculating the number of PCA-coefficients that exhibit substantially simultaneous changes.

18. A portable system as set forth in claim 12 in which said processor detects:
fiducial points indicative of a specific phase of the physiological cycle;

time-aligns the said data using said fiducial points; and
applies said mathematical transformation to extract typical patterns from said time-aligned series of said data.

19. A portable system as set forth in claim 12, said system is suitable for use as a simple diagnostic and screening tool during regular daily activities and during night-time, for analysis of slow, long-term trends in cardiac electromagnetic signals that develop gradually over periods of days-weeks-months, for detection of slow changes and abnormalities in the pattern of at least one of electrocardiographic (ECG), magnetocardiographic (MCG), mechanocardiographic, ballistocardiographic, physical activity, body position, blood pressure, vasomotor activity, respiration, temperature, physiological, and health data, including changes in the heart rate, amplitude, polarity, and duration of P, Q, R, S, T and U waves, ST-segment, and the intervals between the peaks (including PR, QRS, and QT intervals), for periodic personal self-examination for subjects at risk or with a history of cardiovascular disease, for monitoring slow changes in the said data due to development of cardiovascular disease, treatment results, physical exercises, behavioral, environmental, psychophysiological, pharmacological, and health factors.

20. A portable system as set forth in claim 12 which is suitable for analysis of slow changes in the pattern of the signal and representation of the results at different levels of detail using the color-coded scales which are understandable to a lay person and a medical professional.

21. A portable system as set forth in claim 12, in which said different levels of detail include:
    a low-resolution Scale I that represents a small number of primary elements;
    an intermediate-resolution Scale II that represents serial changes in each of the said elements using a mathematical decomposition into series of representative indicators; and
    a high-resolution Scale III that combines serial changes in all elements of the said data to provide complete information about the dynamics of the signal.

22. A portable system as set forth in claim 12 that is wearable, being worn in a pocket or attached to the clothes or a belt or attached using a stripe.

23. A portable system as set forth in claim 22, which includes sensors for measuring at least one of the following signals: a 1, 2, or 3-axial accelerometer, giant magnetic resistance (GMR), or another sensor determining position and movements of the chest and body, and physical activity of a subject, optical light or infra-red sensor for measuring cardiac mechanical activity, sonic or ultra-sonic sensors for measuring heart and lung sounds, blood flow, and blood pressure, non-invasive, non-contact sensors for measuring glucose, hemoglobin, and other biochemical, hormonal, biophysical, respiratory, genetic, proteomic; environmental, and health data.

24. A portable system as set forth in claim 12 that includes:
    a data acquisition unit for measuring at least one of electrocardiographic (ECG), magnetocardiographic (MCG), blood pressure, vasomotor activity, physical activity, body position, respiration, temperature, physiological, and health data;
    a processing unit for collecting the data and extracting the typical patterns; and
    a communication unit for sending the data and receiving information from other devices.

25. A portable system as set forth in claim 24 in which said communication unit is wireless.

26. A portable system as set forth in claim 12, in which said at least one sensor includes at least one of the following sensors: fluxgate, optical, laser-optical, superconducting quantum interference devices (SQUIDs) and non-contact electrocardiographic sensor.

27. A system as set forth in claim 12 in which said processor comprises at least one computer device selected from a specialized computer, a personal computer, a computer organizer (PDA), a cell phone, a smart phone, a group of computers connected via at least one of a local network, wireless network, and the Internet.

28. A system for analysis of serial changes or trends in at least one of electrocardiographic (ECG), magnetocardiographic (MCG), mechanocardiographic, ballistocardiographic, physical activity, body position, respiration, temperature, blood pressure, vasomotor activity, physiological, and health data, said system comprising:
    at least one miniaturized, non-contact sensor for measuring said data from at least one fiducial point; and
    at least one analysis unit for forming a time series from said data obtained from a period of at least several seconds, extracting a typical pattern or waveform or a set of coefficients or wavelets representing characteristic features of the said data during the corresponding time interval using at least one method selected from averaging, mathematical transformation, mathematical modeling, statistical analysis, pattern recognition, and artificial intelligence; forming time series from said typical patterns or waveforms or coefficients or wavelets representing consecutive time intervals, analyzing trends or changes in said time series using a mathematical transformation, characterizing said time series using Principal Component Analysis (PCA), generating PCA-coefficients indicative of changes in the individual pattern, and determining the magnitude of said changes by using time varying mean and variance of said PCA-coefficients and determining the complexity of said linear and nonlinear changes by calculating the number of PCA-coefficients that exhibit substantially simultaneous changes.

29. A system set forth in claim 28 said system comprised of software and hardware for filtering at least one of electrocardiographic (ECG), magnetocardiographic (MCG), mechanocardiographic, ballistocardiographic data, blood pressure, vasomotor activity, physical activity, body position, respiration, temperature, physiological, and health data, rejecting noisy or corrupted data prior to said extraction of typical patterns.

30. A system as set forth in claim 28 in which said mathematical transformation and mathematical modeling includes at least one of the following methods: averaging the signal over a period of at least several cardiac beats (seconds), orthogonal and non-orthogonal decompositions, principal component analysis, mappings and projections, wavelet transform, Fourier transform, Laplace transform, and Hilbert transform, linear and non-linear correlations, linear and non-linear regression models, analysis of variance, cluster analysis, factor analysis, canonical analysis, regression and discriminant function analyses, and probabilistic methods, Bayesian probability and Mahalanobis distance, pattern recognition, methods of artificial intelligence, fuzzy logic, neural networks, expert systems, statistical estimators, filtering techniques, and hybrid artificial intelligence systems.

31. A system as set said forth in claim 28, in which said characterizing uses Principal Component Analysis (PCA) and generating PCA-coefficients indicative of both linear and nonlinear changes in the individual pattern.

32. A system as set forth in claim 28 said detecting of fiducial points is performed by measuring at least one of the following signals: mechanical movements of the chest and other parts of the human body measured by a 1, 2, or 3-axial accelerometer, giant magnetic resistance (GMR), or another sensor determining position and movements of the chest and body, mechanical sounds of the heart, electrical signals generated by the heart, light, infrared, and ultrasound signals measuring cardiac mechanical activity.

33. A system for analysis of serial changes or trends in at least one of electrocardiographic (ECG), magnetocardiographic (MCG), mechanocardiographic, ballistocardiographic, physical activity, body position, respiration, temperature, blood pressure, vasomotor activity, physiological, and health data, said system comprising:
   at least one miniaturized sensor for measuring said data from at least one fiducial point;
   at least one first analysis unit for analyzing said data in low-level-of-detail to extract significant features from monitored signals and compare said features with reference values, said low-level-of-detail analysis applied locally, close to the point of data acquisition; and
   at least one second analysis unit for analyzing said data in a higher-level-of-detail to identify at least one of short-term and long-term trends of changes in said significant features using at least one method selected from mathematical decomposition, modeling, statistical analysis, pattern recognition, and artificial intelligence.

34. A system as set forth in claim 33, said system applied for analysis of slow changes in the pattern of the signal and representation of the results at different levels of detail using the color-coded scales which are understandable to a lay person and a medical professional.

35. A system as set forth in claim 34, in which said different levels of detail include:
   a low-resolution Scale I that represents a small number of primary elements;
   an intermediate-resolution Scale II that represents serial changes in each of the said elements using a mathematical decomposition into series of representative indicators; and
   a high-resolution Scale III that combines serial changes in all elements of at least one of electrocardiographic (ECG), magnetocardiographic (MCG), physical activity, body position, respiration, blood pressure, vasomotor activity, temperature, physiological, and health data to provide complete information about the dynamics of said data.

36. A system as set forth in claim 33 in which:
   the measurement of biomagnetic signals of the heart is performed using at least one of the following magnetometers: fluxgate, optical, laser-optical, and superconducting quantum interference device (SQUID); or
   the measurement of electrocardiographic signals is performed by at least one non-contact sensor.

37. A system as set forth in claim 33 which includes at least one non-contact physiological sensor capable of exchanging information with an implantable device.

38. A system as set forth in claim 37 in which said at least one non-contact physiological sensor is adapted to be implanted under the skin.

39. A system as set forth in claim 33 in which said at least one sensor records at least one signal related to at least one of peripheral, spinal, and cranial neural activity.

40. A system as set forth in claim 33 in which said at least one sensor records at least one signal related to the central (brain) neural activity.

* * * * *